United States Patent
Counts et al.

(10) Patent No.: US 10,463,611 B2
(45) Date of Patent: Nov. 5, 2019

(54) CONTROLLED ABSORPTION WATER-SOLUBLE PHARMACEUTICALLY ACTIVE ORGANIC COMPOUND FORMULATION FOR ONCE-DAILY ADMINISTRATION

(75) Inventors: David F. Counts, Royersford, PA (US); Donald P. Cox, Philipsburg, NJ (US); Anup K. Dam, Hamilton Square, NJ (US); Michael E. Stalhamer, Edison, NJ (US)

(73) Assignee: STI PHARMA, LLC, Newtown, PA (US)

( * ) Notice: Subject to any disclaimer, the term of this patent is extended or adjusted under 35 U.S.C. 154(b) by 0 days.

(21) Appl. No.: 14/119,387

(22) PCT Filed: Jun. 7, 2012

(86) PCT No.: PCT/US2012/041331
§ 371 (c)(1),
(2), (4) Date: Feb. 24, 2014

(87) PCT Pub. No.: WO2012/170676
PCT Pub. Date: Dec. 13, 2012

(65) Prior Publication Data
US 2014/0154313 A1    Jun. 5, 2014

Related U.S. Application Data

(60) Provisional application No. 61/494,659, filed on Jun. 8, 2011.

(51) Int. Cl.
| A61K 9/50 | (2006.01) |
| A61K 31/192 | (2006.01) |
| A61K 9/16 | (2006.01) |
| A61K 9/00 | (2006.01) |

(52) U.S. Cl.
CPC .................................. *A61K 9/0056* (2013.01)

(58) Field of Classification Search
None
See application file for complete search history.

(56) References Cited

U.S. PATENT DOCUMENTS

| 4,828,840 | A | * | 5/1989 | Sakamoto ............ A61K 9/5078 424/474 |
| 4,971,805 | A | | 11/1990 | Kitanishi et al. |
| 5,431,922 | A | | 7/1995 | Nicklasson |
| 5,529,790 | A | * | 6/1996 | Eichel .................. A61K 9/5015 424/409 |
| 5,558,879 | A | | 9/1996 | Chen et al. |
| 5,637,320 | A | * | 6/1997 | Bourke ................ A61K 9/2081 424/451 |
| 5,716,648 | A | | 2/1998 | Halskov et al. |
| 6,528,090 | B2 | | 3/2003 | Qiu et al. |
| 7,101,573 | B2 | * | 9/2006 | Szymczak ............. A61K 9/146 424/464 |
| 2004/0219210 | A1 | | 11/2004 | Guo |
| 2004/0228915 | A1 | * | 11/2004 | Noack et al. ................. 424/471 |
| 2006/0246134 | A1 | * | 11/2006 | Venkatesh ............ A61K 9/2081 424/469 |
| 2007/0160667 | A1 | | 7/2007 | Sherman et al. |
| 2007/0184115 | A1 | | 8/2007 | Mamajiwalla et al. |
| 2008/0026052 | A1 | | 1/2008 | Shoenhard |
| 2010/0008986 | A1 | | 1/2010 | Mehta et al. |
| 2010/0305163 | A1 | | 12/2010 | Yedurkar et al. |
| 2011/0313009 | A1 | * | 12/2011 | Tidmarsh ............. A61K 9/0004 514/370 |

FOREIGN PATENT DOCUMENTS

| EP | 0255404 A1 | 2/1988 |
| EP | 0313328 A1 | 4/1989 |
| EP | 0527637 A1 | 2/1993 |

(Continued)

OTHER PUBLICATIONS

Steele et al. Drug Development and Industrial Pharmacy, vol. 30, No. 1, pp. 103-109; publication year: 2004.*
International Patent Application No. PCT/US2012/041331, International Search Report, dated Aug. 22, 2012, 4 pages.
The Supplementary European Search Report for corresponding EP patent application No. 12797656.1, dated Oct. 7, 2014, 7 pages.
The International Preliminary Report on Patentability for corresponding PCT patent application No. PCT/US2012/041331 dated Dec. 10, 2013, 7 pages.
English-language abstract for JP 2007-039353 (2007).
English-language translation of Office Action dated Mar. 1, 2016 issued in the corresponding Japanese Patent Application No. 2014-514630.
Office Action dated Nov. 11, 2016 issued in corresponding Japanese patent application.

*Primary Examiner* — Katherine Peebles
(74) *Attorney, Agent, or Firm* — Morgan, Lewis & Bockius LLP

(57) ABSTRACT

The present disclosure provides a once-daily water-soluble pharmaceutically active formulation for oral administration. In certain embodiments, the composition comprises a water-soluble pharmaceutically active organic compound incorporated into a small particulate, each particulate having a core of the water-soluble pharmaceutically active organic compound or an acceptable salt thereof in reversible association with a pharmaceutically acceptable drug-binding polymer. The core of the composition being surrounded by an insoluble water permeable membrane that is capable of delaying the dissolution of the pharmaceutically active compound therewithin and providing for extended release of the pharmaceutically active compound. In some embodiments, the formulation of the invention are designed to extend release of the pharmaceutically active organic compound for about 3 hours to about 8 hours, thereby enabling preparation of an extended release formulation for any pharmaceutically active compound with a half-life of from about 16 hours to about 21 hours.

17 Claims, 4 Drawing Sheets

(56) References Cited

FOREIGN PATENT DOCUMENTS

| | | |
|---|---|---|
| JP | 63107917 A | 5/1988 |
| JP | 1250314 A | 10/1989 |
| JP | 5201867 A | 8/1993 |
| JP | 2006522099 A | 9/2006 |
| JP | 200739353 A | 2/2007 |
| JP | 200919056 A | 1/2009 |
| WO | 0018374 A1 | 4/2000 |
| WO | 02098352 | 12/2002 |
| WO | 2004087175 A1 | 10/2004 |
| WO | 2005046652 A1 | 5/2005 |
| WO | 2012170676 | 12/2012 |

\* cited by examiner

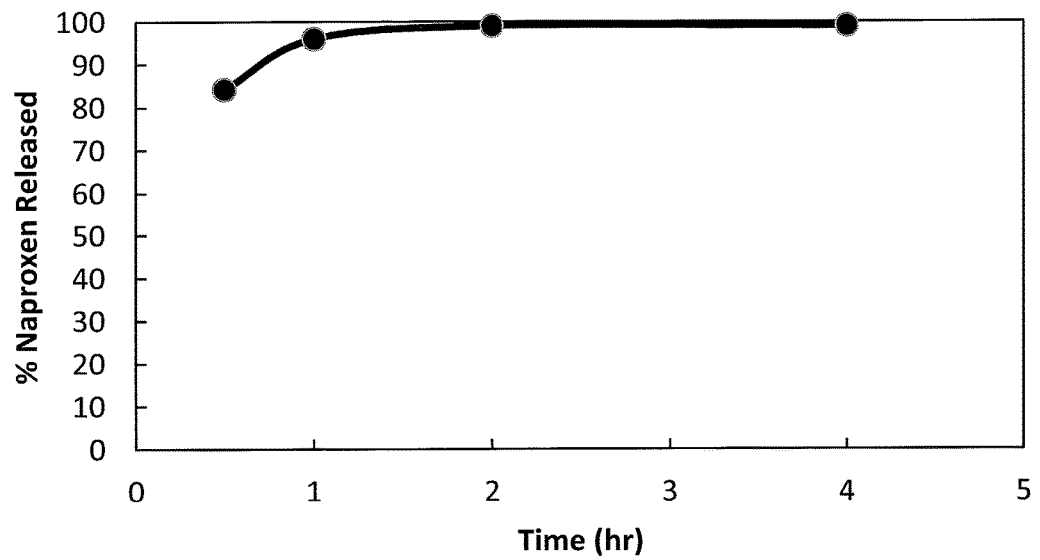
Figure 1. Naproxen Release from Formulation 1
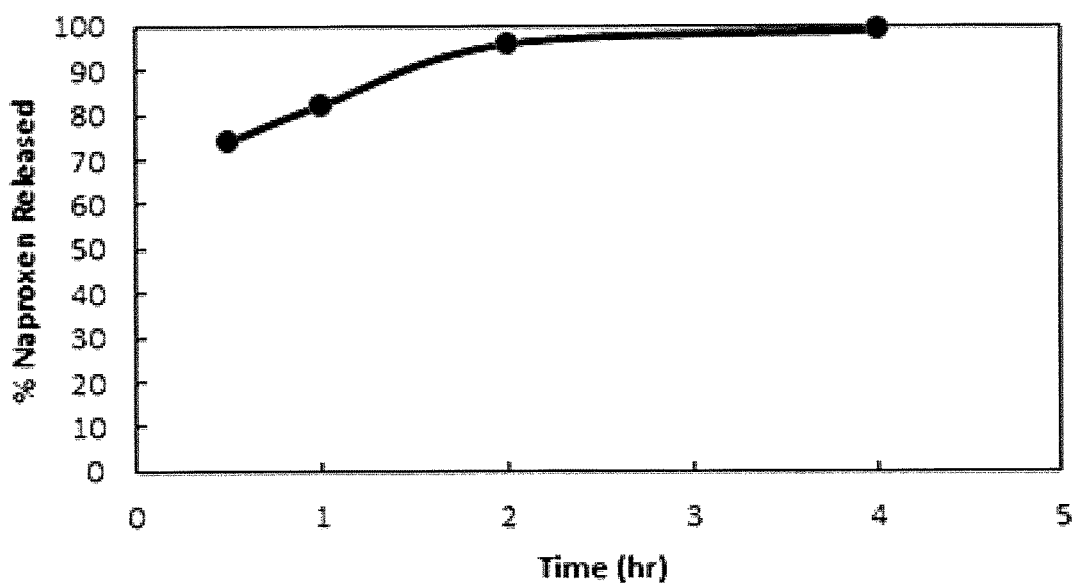
Figure 2. Naproxen Release from Formulation 2

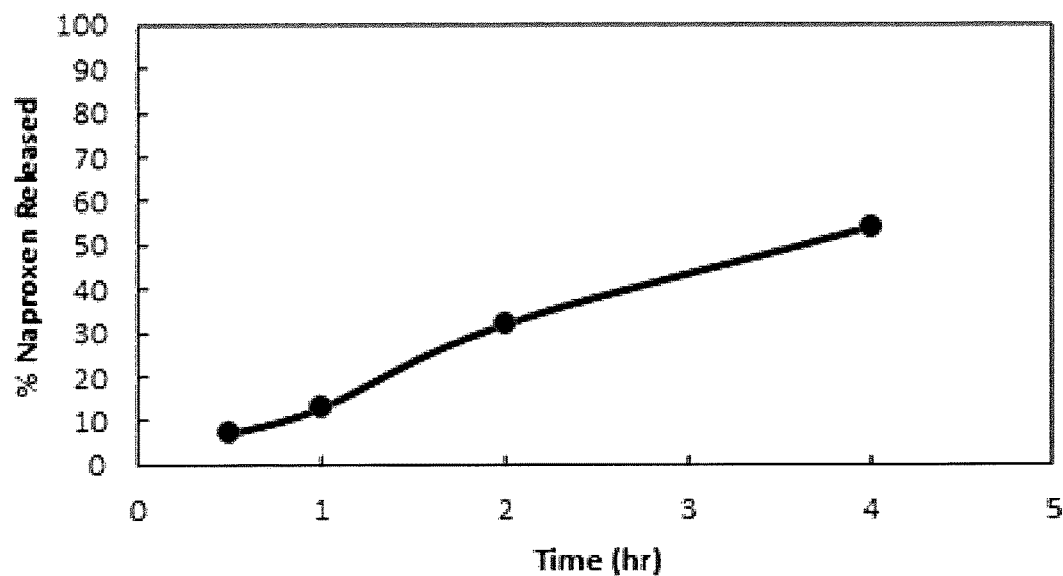
Figure 3. Naproxen Release from Formulation 3
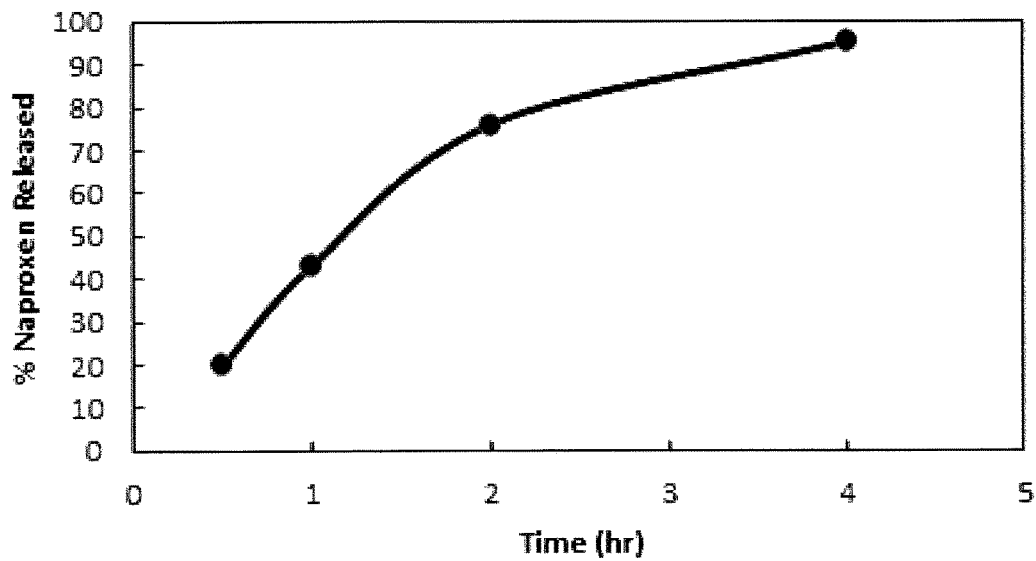
Figure 4. Naproxen Release from Formulation 4

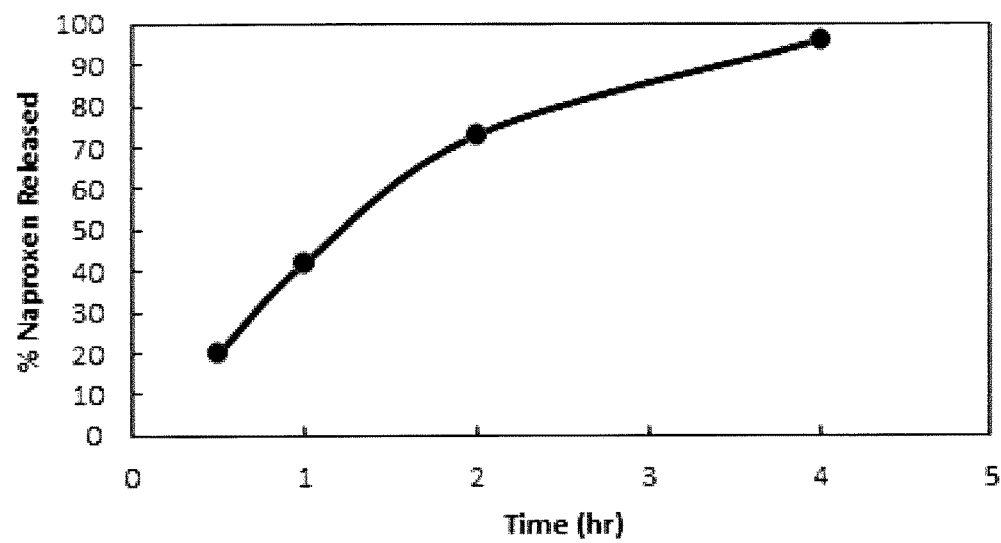
Figure 5. Naproxen Release from Formulation 5
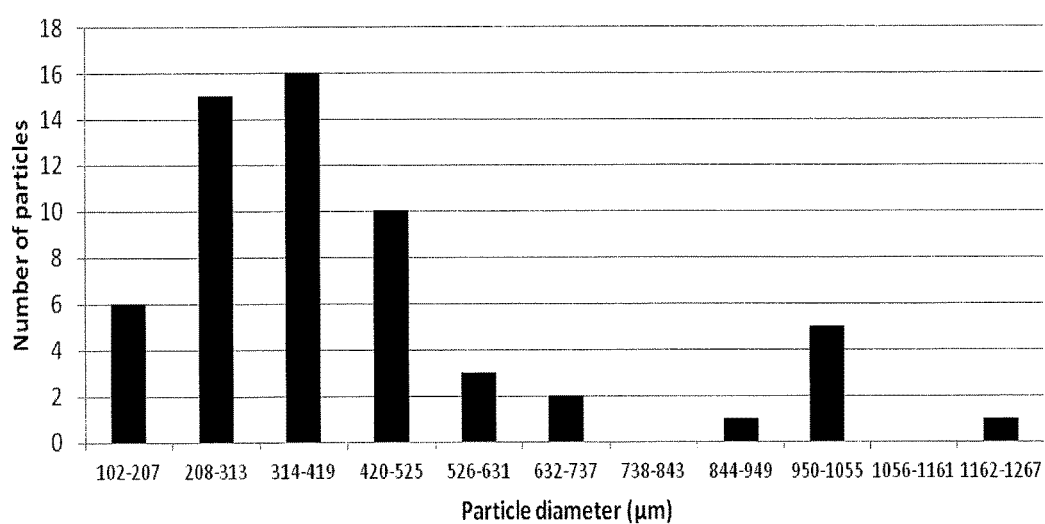
Figure 6. Particle Distribution for Formulation 2 Extended Release Formulation

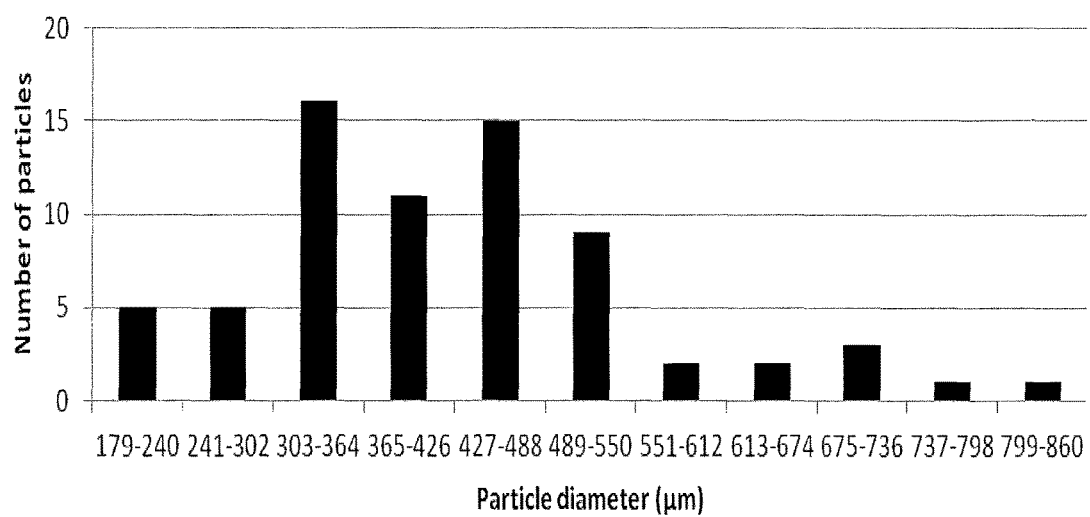
Figure 7. Particle Distribution for Formulation 4 Extended Release Formulation

CONTROLLED ABSORPTION WATER-SOLUBLE PHARMACEUTICALLY ACTIVE ORGANIC COMPOUND FORMULATION FOR ONCE-DAILY ADMINISTRATION

CROSS-REFERENCE TO RELATED APPLICATIONS

The present U.S. patent application is a U.S. National Stage application of international application number PCT/US2012/041331 filed 7 Jun. 2012, which claims priority to U.S. Provisional Patent Application No. 61/494,659 filed 8 Jun. 2011, all of which are incorporated herein by reference in their entireties.

FIELD OF THE INVENTION

This invention relates to a controlled absorption pharmaceutical formulation and, in particular, to a controlled absorption form of pharmaceutically active compounds for oral administration in an easy to swallow particulate formulation suitable for use with an acceptable 'soft food' for those with difficulty in swallowing a tablet, capsule or pill and for administration of pharmaceutically active compounds in a gastro-nasal feeding tube or other "feeding tube" type apparatus where timed release of the active is desired.

BACKGROUND OF THE INVENTION

Many drugs that are water soluble and easily absorbed from the gastrointestinal track could be more advantageously formulated as controlled release once daily oral dosage forms instead of as immediate release dosage forms. Since a standard immediate release formulation is one that is designed to release the drug immediately upon dissolution in the gastrointestinal tract, there are at least two reasons why the switch to controlled release dosage forms would be beneficial. First, pertaining particularly to oral delivery, drugs ingested are passed through the gastrointestinal tract within 24 hours and sometimes in a few hours after ingestion. Second, pertaining to oral and parenteral delivery, the half life of most drugs is less than a day and usually no more than a few hours. Thus, it is very difficult for a standard immediate release single oral dose of a drug to be effective for more than 24 hours and in most cases more than several hours.

Naproxen, for example, is a propionic acid derivative ((S)-6-methoxy-methyl-2-naphthaleneacetic acid), non-steroidal, anti-inflammatory drug (NSAID) that exhibits analgesic and antipyretic properties. Naproxen represents pharmaceutically active compounds which (a) are water soluble and easily absorbed from the gastrointestinal track; (a) would be advantageous to be administered once a day instead of multiple times a day; and (c) are administered to a wide range of patients where an analgesic effect due to the inhibition of inflammation is desired. Many of the effects of naproxen are associated with the inhibition of prostaglandin synthesis and in particular cyclo-oxygenase (COX), a family of enzymes (COX 1 and COX 2 seem to currently be the most medically important), that catalyze the formation of prostaglandin precursors from arachidonic acid (Simmons, D. L. et al., *Pharmacol. Rev.* 2004, 56, pp. 387-437). Inhibition of COX 2 is believed to be effective in blocking the arachidonic acid metabolic pathway that is most responsible for pain and inflammation. Naproxen is used to relieve mild to moderately severe pain in rheumatoid arthritis, osteoarthritis and other inflammatory conditions.

Plasma naproxen concentrations of 30-90 µg/mL are reportedly required for anti-inflammatory or analgesic effects. Plasma naproxen levels between 30-70 µg/mL (Sevelius, H. et al., *Br. J. Clin. Pharmacol.* 1980, 10, pp. 259-263) have been reported to reduce post partum pain. Pain in patients with rheumatoid arthritis suggested that pain reduction in this condition occurred at plasma naproxen levels above 50 µg/mL (Day, R. O. et al., *Clin. Pharmacol, Ther.* 1982, 31, pp. 733-740). Thus, while the rate of absorption may affect the onset of analgesic activity, continued plasma levels of the drug are likely to be important in maintaining analgesia.

Examples of extended release formulations aimed at slowing release of drug as it travels through the gastrointestinal tract include those developed by Elan, Depomed, Alza, Biovail, Pennwest and Kos Pharmaceuticals. These drug delivery systems are based on polymer coatings, hydrogels, polymer foams, osmotic pressure, and other technologies (for a review, see Rosen, H. & T. Arbribat, 2005, Nat. Rev. Drug Discovery, published online Apr. 22, 2005, doi: 10.1038/nrd1721). Other research has focused on the development of prodrugs designed to improve physicochemical, biopharmaceutical or pharmokinetic properties of drugs, including controlling or extending drug release in the body (for a review, see J. Rautio, et al., 2008, Nat. Rev. Drug Discovery Volume 7, March 2008, 255-270).

Notwithstanding the technical advances referred to above, a single dose of an immediate or extended release orally delivered formulation of a drug is almost never effective for at least a day, save a handful of drugs that have very long half lives. Thus, there is a need in the art to develop drug compositions and methods of manufacture that are able to extend the delivery of a single drug dose to beyond one day, and preferably to multiple days. This invention addresses those needs.

BRIEF SUMMARY OF THE INVENTION

In one aspect, the present disclosure provides a particulate composition. In certain embodiments the particulate composition comprises (a) a core, said core comprising a pharmaceutically active substance, said pharmaceutically active substance having an interaction with said set of one or more drug binding polymers having; and (b) a coat, said coat comprising a membrane-forming polymer, said membrane-forming polymer surrounding said core, wherein said pharmaceutically active substance comprises a pharmaceutically active compound, a pharmaceutically acceptable salt of said pharmaceutically active compound or a combination thereof. In some embodiments, the particulate composition comprises (a) an inert core, said inert core comprising a set of one or more drug binding polymers; and (b) a coat, said coat comprising a membrane-forming polymer, said membrane-forming polymer surrounding said core.

In one embodiment, the set of one or more drug binding polymers is selected from the group consisting of ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly (ethylene), poly(ethylene) low density, poly (ethylene) high density, poly(propylene), poly(ethylene oxide), poly(ethylene terephthalate), poly(vinyl isobutyl ether), poly(vinyl acetate), poly(vinyl chloride) or polyurethane and combinations thereof.

In another embodiment, the pharmaceutically active substance and the set of one or more drug binding polymers respectively are present in the core particle in a weight ratio of from about 20:1 to about 1:2 (pharmaceutically active substance:drug binding polymer(s)). In yet another embodiment, the interaction between said pharmaceutically active substance and said set of one or more drug binding polymers comprises chemical bonding, ionic bonding, complexation, van der Waals interaction, hydrogen bonding, or combinations thereof. In another embodiment, at least one of the set of one or more drug binding polymers is insoluble in water. In yet another embodiment, at least one of the set of one or more drug binding polymers is soluble in water. In a further embodiment, the coat comprises a water-insoluble, water-permeable polymer capable of retarding drug release.

In one embodiment, the core comprises a powder, the powder comprising particles of the pharmaceutically active substance mixed with particles of the set of one or more drug binding polymers, and wherein the coat comprises a water-insoluble, water-permeable polymer. In a further embodiment, the core comprises a powder, the powder comprising particles of the pharmaceutically active substance mixed with particles of the set of one or more drug binding polymers, wherein the set of one or more drug binding polymers comprise at least one pharmaceutically acceptable water insoluble polymer, and wherein the coat comprises a water-insoluble, water-permeable polymer.

In another embodiment, a particulate composition according with the present invention comprises microparticles/microparticulates having average diameter of from about 100 μm to about 900 μm.

In another aspect, the present disclosure provides a method of making a particulate composition. In certain embodiments, the method comprises (a) blending a powder, the powder comprising particles of a pharmaceutically active substance and particles of a set of one or more polymers, to form a homogenous powder blend; (b) shaping a portion of the homogenous powder blend to form a central core; and (c) applying a polymer binding solution to the central core to form a layered structure on the central core. In an embodiment, the pharmaceutically active substance comprises a pharmaceutically active compound, a pharmaceutically acceptable salt of the pharmaceutically active compound or a combination thereof.

In one embodiment, the method of making a particulate composition comprises (a) blending a powder, the powder comprising particles of a set of one or more polymers, to form a homogenous powder blend; (b) shaping a portion of the homogenous powder blend to form a central inert core; and (c) applying a polymer binding solution to the central inert core, to form a layered structure on the central inert core.

In yet another aspect, the present disclosure provides an oral pharmaceutical sustained release composition. In some embodiments, the oral pharmaceutical sustained release composition comprises the particulate composition in accordance with the present invention. In a further embodiment, the oral pharmaceutical sustained release composition has a dissolution rate which when measured in a type 1 dissolution basket apparatus according to U.S. Pharmacopoeia XXII in phosphate buffer at pH 7.2 and at 75 r.p.m. corresponds to the following dissolution pattern:

(a) from 15 to 30% of the total pharmaceutically active chemical is released after 0.5 hours of measurement in said apparatus;

(b) from 25 to 60% of the total pharmaceutically active chemical is released after 1 hour of measurement in said apparatus; and (c) not less than 65% of the total pharmaceutically active chemical is released after 4 hours of measurement in said apparatus.

In an embodiment, a pharmaceutical formulation in accordance with the present invention comprises a microparticulate composition as described herein filled into capsules or compressed into tablets. In another embodiment, a pharmaceutical formulation in accordance with the present invention comprises a microparticulate composition as described herein filled into capsules. In another embodiment, a pharmaceutical formulation in accordance with the present invention comprises a microparticulate composition as described herein compressed into tablets. In another embodiment, said capsules or said tablets rapidly dissolve in any aqueous medium to release microparticulates of said particulate composition. In yet another embodiment, a pharmaceutically active substance contained in said particulate composition is released in a controlled manner. In another embodiment, said pharmaceutically active substance is released in a controlled manner having a release profile that is substantially the same/identical to the release profile of said microparticulates alone.

In another aspect, the present disclosure provides a method for extending delivery of a single dose of a pharmaceutically active substance to once daily or to beyond one day from administration of the dose to a subject. In an embodiment, the method for extending delivery of a single dose of a pharmaceutically active substance comprises (a) blending powder particles of the pharmaceutically active substance with powder particles of a set of one or more polymers to form a homogenous powder blend, wherein the a pharmaceutically active substance comprises a pharmaceutically active compound, a pharmaceutically acceptable salt of the pharmaceutically active compound or a combination thereof; (b) shaping a portion of the homogenous powder blend to form a central core; and (c) applying a polymer binding solution to the central core to form a layered structure on the central core to form a pharmaceutical composition, wherein the pharmaceutical composition delivers the pharmaceutically active substance to the subject for at least one or more days from administration of a single dose of the pharmaceutical composition.

Other features and advantages of the invention will be understood by reference to the drawings, detailed description and examples that follow.

BRIEF DESCRIPTION OF DRAWINGS

The foregoing summary, as well as the following detailed description of embodiments of the particulate composition, methods of making and using the composition, and controlled release pharmaceutical composition for controlled delivery of drugs, will be better understood when read in conjunction with the appended drawings of exemplary embodiments. It should be understood, however, that the invention is not limited to the precise arrangements and instrumentalities shown.

In the drawings:

FIG. 1 is a graph illustrating percent naproxen released from a formulation in accordance with exemplary Formulation 1, described in the Examples Section, when tested by the method of the U.S. Pharmacopoeia XXII Basket method in phosphate buffer at pH 7.2 and at 75 r.p.m. versus time (hours);

FIG. 2 is a graph illustrating percent naproxen released from a formulation in accordance with exemplary Formulation 2, described in the Examples Section, when tested by the method of the U.S. Pharmacopoeia XXII Basket method in phosphate buffer at pH 7.2 and at 75 r.p.m. versus time (hours);

FIG. 3 is a graph illustrating percent naproxen released from a formulation in accordance with exemplary Formulation 3, described in the Examples Section, when tested by the method of the U.S. Pharmacopoeia XXII Basket method in phosphate buffer at pH 7.2 and at 75 r.p.m. versus time (hours);

FIG. 4 is a graph illustrating percent naproxen released from a formulation in accordance with exemplary Formulation 4, described in the Examples Section, when tested by the method of the U.S. Pharmacopoeia XXII Basket method in phosphate buffer at pH 7.2 and at 75 r.p.m. versus time (hours);

FIG. 5 is a graph illustrating percent naproxen released from a formulation in accordance with formulation 5, described in the Examples Section, when tested by the method of the U.S. Pharmacopoeia XXII Basket method in phosphate buffer at pH 7.2 and at 75 r.p.m. versus time (hours);

FIG. 6 illustrates particle size distribution for Formulation 2; and

FIG. 7 illustrates particle distribution for Formulation 4.

DETAILED DESCRIPTION OF THE INVENTION

All references, including publications, patent applications, and patents, cited herein are hereby incorporated by reference to the same extent as if each reference were individually and specifically indicated to be incorporated by reference and were set forth in its entirety herein.

As used herein, the terms "drug," "biologically active substance," and the like, are used interchangeably herein to refer to a substance, or a composition containing one or more substances, having a biological activity or therapeutic effect in a human or animal.

Half life is defined as the time that it takes for 50% of the dosage absorbed into the body to be excreted from the body.

The terms "patient," "subject" or "individual" are used interchangeably herein and refer to a human or an animal that is the object of treatment, observation or experiment, inasmuch as the present invention is contemplated to have utility in human and veterinary medicine.

A single dose or single administration is defined as the dose of a drug that is delivered at approximately the same time and can be composed of one or more capsules or tablets, liquids, powders, dispersions, and the like.

As used herein, a "therapeutically effective amount" or an "effective amount" or an "efficacious amount" is the amount of a substance or composition sufficient to provide a beneficial effect to the individual to whom the substance or composition is administered.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

A. Biologically Active Compounds:

Suitable biologically active substances that can be used with the methods and compositions of the present invention can be of any class of substances, including anesthetics, antidiabetic, bone metabolic modulators, cardiovascular agents, central nervous system depressants, gastrointestinal agents, antibiotics, antivirals, antiinfectives, antibacterials, antineoplastics, hormones, steroid agents, antiparkinsonian, contraceptive, erectile dysfunction agents, analgesics, pain medications, anti-inflammatories, antilipidemic agents, diagnostic agents, antihistamines, peptide and proteins, urinary tract agents, psychotherapeutics, osteoporosis medications, immunomodulators and antiasthmatics.

Non-limiting examples of suitable pharmaceutically active substances for use with the methods and compositions include abacavir, abamectin, abanoquil, abaperidone, abarelix, abecamil, abiraterone, abitesartan, ablukast, abunidazole, acadesine, acamprosate, acaprazine, acebrochol, acebutolol, acecamide, acecarbromal, aceclidine, aceclofenac, acedapsone, acediasulfone, acedoben, acefluranol, acefurtiamine, acefylline clofibrol, acefylline piperazine, aceglatone, aceglutaminde, acemetacin, aceneuramicacid, acenocoumarol, acepeprone, acepromazine, acepromazine, acequinoline, acesulfame, acetaminosalol, acetanilide, acetarsone, acetaminophen, acetazolamide, acetiamine, acetiromate, acetohexamide, acetophenazone, acetophenetidin, acetorphine, acetosulfone, acetriozoic acid, acetylcysteine, acetyldigitoxin, acetylleucine, acetyltributyl citrate, acetyltriethyl citrate, acevaltrate, acexamin acid, acifran, acipimox, acitazanolast, acitemate, acitretin, acivicin, alcantate, aclarubicin, aclatonium napadisilate, acolbifene, aconiazide, aconitine, acotiamide, acoxatrine, acreozast, acridorex, acriflavine, acrihellin, acrisorcin, acrivastine, acroinonide, acronine, actaplanin, actarit, actinoquinol, actisolide, actodigin, acyclovir, adafenoxate, adamexine, adapalene, adaprolol, adatanserin, adefovir, adekalant, adelmidrol, ademitrionine, adenosine, adibendal, adicillin, adimolol, adinazolam, adiphenine, aditeren, aditoprim, adosopine, adozelesin, adrafinil, adrenalone, adrogolide, afalanine, afeletecan, afloqualone, afovirsen, afurolol, aganodine, aglepristone, agomelatine, aklomide, alacepril, alafosfalin, alagebrium, alamecin, alamifovir, alanine, alanosine, alaproclate, alatrofloxacin, alazanine triclofenate, albaconazole, albendazole, albuterol, albutoin, alclofenac, alclometasone, alcloxa, alcuronium, aldioxa, aldosterone, alemcinal, alendronic acid, alentemol, alepride, alestramustine, aletamine, alexidine, alexitol, alexomycin, alfacalcidol, alfadex, alfidalone, alfaprostol, alfatradiol, aldaxalone, alfentranil, alfluzosin, algeldrate, algestone, alibendol, aliconazole, alifedrine, alifurane, alilusem, alimadol, alinastine, alinidine, alipaminde, aliskiren, alitame, alitretinoin, alizapride, alletorphine, allobarbitol, allocamide, allocupreide, allomethadione, allopurinol, allylestrenol, allylprodine, almecillin, almestrone, alminoprofen, almitrine, almokalant, almotriptan, almoxatone, almurtide, alnespirone, alniditan, alonacic acid, alonimid, aloracetam, alosetron, alovudine, aloxidone, aloxiprin, aloxistatin, alozafone, alpertine, alphamepropdine, alphamethadol, alphamethyldopa, alphaprodine, alpidem, alpiropride, alprafenone, alprazolam, alprenolol, alprenoxime, alprostadil, alrestatin, altanserin, altapizone, alteconazole, althiazide, altinicline, altoqualiine, altrenogast, altretamine, alvemeline, alverine, alvimopan, alvocidib, amadinone, amafalone, amanozine, amantadine, amantocillin, ambamustine, ambasilide, ambazone, ambenonium, ambenoxan, ambomycin, ambrisentan, ambroxol, ambruticin, ambucaine, ambucetamide, ambuphylline, ambuside, ambutonium, amcinafal, amcinafide, amcinonide, amdinocillin, amdoxovir, ambucort, amedalin, amelometasone, ameltolide, amelubant, amesergide, ametantrone, amethocaine, amezapine, amezinium, amfenac, amfepentorex, amfetaminil, amflutizole, amfonelic, amicarbalide, amicloral, amicycline, anidantel, amidapsone, amidephrine, amiflamine, amifloverine, amifloxacin, amifostine, amiglumide, amikacin, amikhelline, amiloride, amiloxate, aminacrine, amindocate, amineptine, aminoglutethimide, aminohippuric acid, aminolevulinic acid, aminometradine, aminopentamide, aminophenazone, aminophylline, aminopromazine, aminopterin, aminopyrine, aminoquinol, aminoquinuride, aminorex, aminosalicylic acid, aminothiazole, amiodarone, amiperone, amphenazole, amipizone, amiprolose, amiquinsin, amisometradine, amisulprode, amiterol, amithiozone, amitivir, amitraz, amitriptyline, amitriptyinoxide, amixetrine, amlexanox, amlintide, amlodipine, amocarzine, amodiaquine, amolanone, amonafide, amoproxan, amopyroquine, amorolfine, amoscanate, amosulatol, amotosalen, amotriphene, amoxapine, amoxecaine, amoxicillin, amoxydramine, amperozide, anphechloral, amphenidone, amphetamine, amphomycin, amphotalide, amphotericin, ampicillin, ampiroxicam, amprenavir, amprolium, ampyrimine, ampyzine, amquinate, amrubicin, amsacrine, amtolmetin, amustaline, amylobarbital, angestone, anagrelide, anakinra, anaritide, anastrozole, anatibant, anaxirone, anazocine, anazolene, ancarolol, ancitabine, andolast, androstenediol, androstenedione, andulafungin, anecortave, anetholtrithion, angiotensin amide, andidoxamine, anidulafungin, anilamate, anileridine, anilopam, anipamil, aniracetam, anirolate, anisacril, anisindione, anisopirol, anisotropine, anisperimus, anitrazafen, anpirtoline, ansoxetine, antafenite, antazoline, antazonite, anthelmycin, anthralin, anthramycin, antipyrine, antrafenine, apadoline, apafant, apalcillin, apaxafylline, apaziquone, apazone, apicycline, aplindore, apomorphine, apovincamine, apraclonidine, apramycin, aprepitant, aprakalim, aprindine, aprinocarsine, apofene, aprosulate, aptazapine, aptiganel, aptocaine, aranidipine, aranotin, arbaprosil, arbekacin, arbutamine, arclofenin, ardacin, ardeparin, arecoline, arfalasin, arfendazam, arformoterol, argatroban, argimesna, argipressin, argiprestocin, arlidone, arimoclomol, aripiprazole, armodafinil, arnolol, arofylline, artinolol, arprinocid, arpromidine, arsanilic acid, arteflene, artemether, artemisinin, artemotil, artenimol, artesunate, articaine, artilide, arundic acid, arzoxifene, ascorbic acid, arsenapine, aseripide, asimadoline, asobamast, asocainol, asoprisnil, aspartame, aspartocin, asperlin, aspirin, aspoxicillin, astemizole, astromicin, asulacrine, atamestane, ataprost, ataquimast, atavanavir, atenolol, atevirdine, atiprone, atilmotin, atipamezole, atipromod, atiprosin, atizoram, atliprofen, atocalcitol, atolide, atomoxetine, atorvastatin, atosiban, atovaquone, atracurium, atrasentan, atraleuton, atrimustine, atrinositol, atromepane, atropine, atropine oxide, auranofin, aurothioglucose, avanafil, avasimibe, avicatonin, avalamycin, aviptadil, avitriptan, avizafone, avobenzone, azoparcin, avorelin, pyridine, axamozide, axitirome, axomadol, azabon, azabuperone, azacitidine, azacitidine, azaclorzine, azaconazole, azacosterol, azacyclonol, azaftozine, azalanstat, azalomycin, azaloxan, azamethiphos, azamethonium, azamulin, azanator, azanidazole, azaperone, azapetine, azaquinzole, azaribine, azarole, azaserine, azasetron, azaspirium, azastene, azatadine, azathioprine, azelaic acid, azelastine, azelinnidipine, azepexole, azepindole, azetepa, azetirelin, azidamfenicol, azidocillin, azimexon, azimilide, azintamide, azipramide, azithromycin, azlocillin, azlocillin, azolimine, azosemide, aztomycin, aztreonam, azumolene, bacampicillin, bacitracin, baclofen, bacmecillinam, bakeprofen, balaglitazone, balazipone, balofloxacin, balsalazide, bamaluzole, bamaquimast, bambermycin, bambuterol, bamethan, bamifylline, bamipine, bamirastine, bamidazole, banoxantrone, baquiloprim, barbexaclone, barbital, barixibat, barmastine, barnidipine, barucamide, barusiban, basifungin, batalbulin, batanopride, batebulast, batelapine, batilol, batimastat, batoprozine, baxitoizine, bazedoxifene, bazinaprine, becanthone, becatecarin, beciparcil, beclamide, becliconazole, beclobrate, beclomethasone, beclotiamine, befetupitant, befiperide, befloxatone, befunolol, befuraline, bekanamycin, belaperidone, belarizine, belfosdil, belotecan, beloxamide, beloxepin, bemarinone, bemegride, bemesetron, bemetizide, beminafil, bemiparin, bemetradine, bemoradan, bemotrizinol, benactyzine, benafentrine, benapryzine, benaxibine, benazepril, bencianol, bencisteine, benclonidine, bencyclane, bendacalol, bendamustine, bendazac, bendazol, benderizine, bendroflumethazide, benethamine penicillin, benexate, benfluorex, benfosformin, benfotiamine, benfluorodil, benhepazone, benidipine, benmoxin, benolizime, benorilate, benorterone, benoxifos, benoxaprofen, benoxinate, benpenolisin, benperidol, benproperine, benrixate, bensalan, benserazide, bensuldazic acid, bentazepam, bentemazole, bentiamine, bentipimine, bentiromide, bentoquatam, benurestat, benzalkonium, benzarone, benzbromarone, benzestrol, benzethidine, benzethonium, benzetimide, benzilonium, benzindopyrine, benziodarone, benzmalecene, benznidazole, benzobarbital, benzocaine, benzoclidine, benzoctamine, benzodepa, benzododecinium, benzonatate, benzopyrronium, benzoquinonium, benzotript, benzoxiquine, benzoxonium, benzoylpas, benzphetamine, benzpiperylon, benzpyrinium, benzquercin, benzquinamide, benzthiazide, benztropine, benzydamine, benzylhydrochlorothiazide, benzylpenicillin, benzylsulfamide, bepafant, beperidium, bephenium, bepiastine, bepridil, beractant, beraprost, berberine, berefrine, bergenin, berlafenone, bermoprofen, bertosamil, berupipam, bervastatin, berythromycin, besigomsin, besipirdine, besonprodil, besulpamide, besunide, beta carotene, betacetylmethadol, betahistine, betaine, betameprodine, betamethadol, betamethasone, betamicin, betamipron, betaprodine, betaxolol, betazole, bethanacol, bethanidine, betiatide, betoxycaine, bevantolol, bevonium, bexarotene, bexlosteride, bezafibrate, beztiramide, bialamicol, biapenem, bibezonium, bibrocathol, bilcalutamide, bicifadine, bicoldil, biclofibrate, biclotymol, bicozamycin, bidimazium, bidisomide, bietamiverine, bietaserpine, bifemelane, bifepramide, bifeprofen, bifeprunox, bifluranol, bifonazole, bilastine, bimakalim, bimatoprost, bimoclomol, bimosiamose, bindarit, binedaline, binfioxacin, binfibrate, biniramycin, binizolast, binodenosine, binospirone, bioallethrin, botin, bipenamol, biperiden, biphenamine, biricodar, biriperone, bisacodyl, bisantrene, bisaramil, bisbendazole, bisbentiamine, bisbutiamine, bisdequilinium, bisfenazone, bisfentidine, bisnafide, bisorbin, bisoctriazole, bisoprolol, bisorcic, bisoxatin, bispyrithione, bithonol, bithionoloxide, butipazone, bitolterol, bitoscanate, bivalirudin, bizelesin, bleomycin, blonanserine, bluensomycin, bofumustine, bolandiol, bolasterone, bolazine, boldenone, bolenol, bolmantalate, bometolol, bopindolol, bornaprine, bornaprolol, borelone, borocaptane, bortezomib, bosentan, botiacrine, boxidine, brallobarbital, brasofensine, brazergoline, brefonalol, bremazocine, brequinar, bretazenil, bretylium, brifentanil, brimonidine, brinazaprone, brindoxime, brinzolamide, brivudine, brobactam, broclepride, brocrestine, brocrinat, brodimoprim, brofaromine, brofoxine, brolaconazole, brolamfetamine, bromadoline, bromamid, bromazepam, bromchlorenone, bromebric acid, bromerguride, brometenamine, bromfenac, bromhexene, bomindione, bromisovalum, bromociclen, bromocriptine, bromodiphenylhydramine, bromofenfos, bromofos, bromopride, bromoxanide, bromperidol, brompheniramine, broparestrol, broperamol, bropirimine, broquinaldol, brosotaminde, brostallicin, brosuximide, brotianide, brotizolam, brovanexine, brovincamine, broxaldine, broxaterol, broxitalamide, broxuridine, broxyquinoline, bucamide, bucetin, buciclovir, bucillamine, bucindolol, bucladesine, buclizine, buclosamide, bucloxic acid, bucolme, bucricaine, bucromarone, bucumolol, budesonide, budipine, budotitane, budralazine, bufenadrine, bufeniode, bufetolol, bufexamac, bufezolac, bufromedil, bufogentin, buformin, bufrolin, bufuralol, bufylline, bulaquine, bumadizone, bumecaine, bumepidil, bumetanide, bumetriazole, bunaftine, bunamidine, bunamiodyl, bunaprolast, bunazosin, bunitrolol, bunolol, buparvaquone, bupicomide, bupivacaine, bupranolol, buprenorphine, bupropion, buquinerin, buquinolate, buquiterine, buramate, burodiline, buserelin, buspirone, busulfan, butobarbital, butacaine, butacetin, butaclamol, butadiazamide, butafosfan, butalamine, butalbital, butamben, butamirate, butamisole, butamoxane, butanilicaine, butanserin, butantrone, butaperazine, butaprost, butaverine, butedronate, bytenafine, buterizine, butenamate, buthiazide, butibufen, butifrine, butikacin, butilfenin, butinazocine, butinoline, butirosin, butixirate, butixocort, butobendine, butoconazole, butocrolol, butoctamide, butofiolol, butonate, butopamine, butopiprine, butoprozine, butopyrammonium, butorphanol, butoxamine, butoxylate, butriptyline, butropium, butylscopolamine, butynamine, buzepide, cabastine, cabergoline, cactinomycin, cadralazine, cadrofloxacin, cafaminol, cafedrine, caffeine, calcifediol, calciprotriene, calcitriol, calcobutrol, caldaret, caldiamine, caloxetic acid, calteridol, clausterone, camazepam, cambendazole, camaglibose, camiverine, camptothecin and its analogues such as 9-amino camptothecin, 10-hydroxy camptothecin, 7-ethyl-10-hydroxy camptothecin, 9-nitro camptothecin and all other camptothecin analogues with six, seven and eight membered lactone rings, camonagrel, camostat, camylofin, canbisol, candesartan, candicidin, candocuronium, candoxatril, candoxatrilat, canertinib, canfosfaminde, cangrelor, cannabinol, canrenoate, canrenone, capecitabine, capobenate, capobenic acid, capravirine, capreomycin, capromorelin, caproxamine, capsaicin, captamine, captodiame, captopril, capuride, carabersat, caracemide, carafiban, caramiphen, carbachol, carbadox, carbamazepine, carbentel, carbasone, carbaspirin, carbazeran, carbazochrome, carbazocine, cabenicillin, carbenoxolone, carbenzide, carbetapentane, carbetocin, carbidopa, carbimazole, carbinoxamine, carbiphene, carbofenotion, carboplatin, carboprost, carboquone, carbubarb, carburazepam, carbutamide, carbuterol, carcainium, carebastine, carfentanil, carfimate, cargutocin, cariporide, carisoprodol, carmantadine, carmofur, carmoterol, carmustine, camidazole, carnitine, carocamide, caroverine, caroxazone, carperidine, carperitide, carperone, carphenazine, carpindolol, carpipramine, carprazidil, carprofen, capronium, carsalam, carsatrin, cartasteine, cartazolate, carteolol, carubicin, carumonam, carvedilol, carvotroline, carzelesin, carzenide, casanthranol, casokefaminde, caspofungin, cathine, cathinone, cebaracetam, cedefingol, cefaclor, cefadroxil, cefalonium, cefaloram, cefamandole, cefaparole, cefatriazine, cefazaflur, cefazedone, cefazolin, cefbuperazone, cefanel, cefcapene, cefclidin, cefdaloxime, cefdinir, cefditoren, cefedrolor, cefempidone, cefepime, cefetamet, cefetecol, cefetriaole, cefivtril, cefixime, cefmatilen, cefmenoxine, cefmepidium, cefmetazole, ceminox, cefodizime, cefonicid, cefoperazone, ceforanide, cefoselis, cefotaxime, cefotetan, cefotiam, cefovecin, cefoxazole, cofoxitin, cefozopran, cefpimizole, cefpiramide, cefpodoxime, cefprozil, cefquinome, cefrotil, cefroxadine, cefsulodin, cefsumide, ceftazidime, cefteram, ceftezole, ceftibuten, ceftioflur, ceftiolene, ceftioxide, ceftioxime, ceftriaxone, cefuracetamime, cefuroxime, cefuzonam, celecoxib, celgosivir, celiprolol, cemadotin, cephacetrile, cephadrine, cephalexin, cephaloglycin. Cephaloridine, cephalothin, cephapirin, cepharanthine, cephradine, cericlamine, cerivastatin, ceronapril, ceruletide, cetaben, cetalkonium, cetamolol, cetefloxacin, cethexonium, cethromycin, cetiedil, cetilistat, cetirizine, cetocycline, cetopheincol, cetotiamine, cetoxime, cetraxate, cetrimonium, cetylpyridinium, cevimeline, chaulmosulfone, chenodiol, chinofon, chlofibrate, chlophendianol, chloracyzine, chloralose, chlorambusil, chloramines-T, chloramphenicol, chlorazanil, chlorbenoxamine, chlorbetamide, chlorcyclizine, chlordantoin, chlordiazepoxide, chlordimorine, chlorhexidine, chlorindanol, chlorisondamine, chloramadione, chlormerodrin, chlormezanone, chlormidazole, chlornaphazine, chloroazodin, chloroprednisone, chloroprocaine, chloropyramine, chloroquine, chloroserpidine, chlorothen, chlorothiazide, chlorotrianisene, chloroxine, chloroxylenol, chlorphenesin, chlorpheniramine, chlorphenoctium, chlorphenoxamine, chlorphentermine, chlorproethazine, chlorproguanil, chlorpromazine, chlorpropamide, chlorprothixene, chlorpyrifos, chlortetracycline, chlorthalidone, chlorthenoxazine, chlorzoxazone, cholecalciferol, cholesterol, choline alfoscerate, choline, chromic chloride, chromonar, ciadox, ciaftalan, ciamexon, cianergoline, cianidanol, cianopramine, ciapilome, cicaprost, cicarperone, ciclactate, ciclafrine, ciclazindol, ciclesonide, clcletanine, cicliomenol, ciclonicate, ciclonium, ciclopirox, ciclopramine, cicloprofen, cicloprolol, ciclosidomine, ciclotizolam, ciclotropium, cicloxilic acid, cicloxolone, cicortonide, cidofovir, cidoxepin, cifenline, cifostodine, ciglitazone, ciheptolane, ciladopa, cilansertron, cilastatin, cilazapril, cilengitide, cilexin, cilnidipine, cilobamine, cilobradine, cilofungin, cilomilast, cilostamide, cilostazol, ciluprevir, cilutazoline, cimaterol, cimemoxin, cimetidine, cimetropium, cimicoxib, cimoxatone, cinacalcet, cinalukast, cinametic acid, cinamolol, cinanserin, cinaproxen, cinchophen, cinecromen, cinepazet, cinepazide, cinfenine, cinfenoac, cinfiumide, cingestol, cinitapride, cinmetacin, cinnamaverine, cinnamedrine, cinnarizine, cinnofuradione, cinoctramide, cinodine, cinolazepam, cinoquidox, cinoxacin, cinoxate, cinoxolone, cinoxopazide, cinperene, cinprazole, cinpropazide, cinpromide, cintazone, cintriamide, cinuperone, cioteronel, cipamfylline, cipemastat, ciprafamide, cipralisant, ciprazafone, ciprefadol, ciprocinonide, ciprofibrate, ciprofloxacin, ciprokiren, cipropride, ciproquazone, ciprestene, ciramadol, cirazoline, cirolemycin, cisapride, cisatracurium, cinconazole, cismadinone, cisplatin, cistinexine, citalopram, citatepine, citenamide, citenazone, citicoline, citiolone, cizolirtine, cladribine, clamidoxic acid, clamikalant, clamoxyquin, clanfenur, clanobutin, clantifen, clarithromycin, clavulanate, clazolam, clazolimine, clazuril, clebopride, clefamide, clemastine, clemeprol, clemizole, clenbuterol, clenpirin, clentiazem, cletoquine, clevidipine, clevudine, clibucaine, clidafidine, clidanac, clindium, climazolam, climbazole, climiqualine, clinafloxacin, clindamycin, clinofibrate, clinolamide, clinprost, clioquinol, clioxanide, cliprofen, cliropamine, clobazam, clobenoside, clobenzepam, clobenorex, clobenztropine, clobetasol, clobetasone, clobutinol, clobuzarit, clocanfamide, clocapramine, clociguanil, clocinizine, clocortolone, clocoumarol, clodacaine, clodanolene, clodazon, clodoxopone, clodronate, clofarabine, clofazimine, clofenamic acid, clofeniclan, clofenetamine, clofenoxyde, clofevine, clofexamine, clofezone, clofibrate, clofibric acid, clofibride, clofilium, clofucarba, clofoctol, cloforex, clofurac, clogestone, cloguanamil, clomacrin, clomegestone, clometacin, clometherone, clomethiazole, clometocillin, clomifenoxide, clominorex, clomiphene, clomipramine, clomocycline, clomoxir, clonazepam, clonazoline, clonidine, clonitazine, clonixeril, clonixin, clopamide, clopenthixol, cloperastine, cloperidone, clopidogrel, clopidol, clopimozide, clopipazan, clopirac, cloponone, cloprendol, cloprostenol, cloprothiazole, cloquinate, cloquinozine, cloracetadol, cloranolol, clorazepate, clorazepic acid, clorethane, chlorexolone, clorfenvinos, clorgiline, cloricromen, cloridarol, clorindanic acid, clorindione, clormecaine, cloroperone, clorophene, cloroqualone, clorotepine, clorprenaline, clorsulon, clortermine, closantel, closiramine, clostebol, clothiapine, clothixamide, clotiazepam, cloticasone, clotioxone, clotixamide, clotrimazole, clovoxamine, cloxacepride, cloxacillin, cloxazolam, cloxestradiol, cloximate, cloxotestosterone, cloxypendyl, cloxyquin, clozapine, cobalamide, cocaine, codeine, codoxime, cofistatin, cogazocine, colchicines, colestolone, colfenamate, colforsin, colfosceril, colimecycline, colterol, coluracetam, conessine, congazone, conivaptan, conorphone, cormethasone, corticorelin, cortisone, cortisuzol, cortivazol, cortodoxone, cotinine, cotriptyline, coumaphos, coumazolin, coumermycin, coumetarol, creatinine, creatinolfosfate, cresotamide, cridanimod, crilvastin, crisnatol, crobenetine, croconazole, cromakalim, cromitrile, cromoglicate lisetil, cromolyn, crolom, cronidipine, cropropamide, crotamiton, crotetamide, crotoniazide, crotoxyfos, crufomate, cuprimyxin, cuproxoline, cyacetacide, cyamemazine, cyanocobalamine, cyclacillin, cyclamate, cyclamic acid, cyclandelate, cyclarbamate, cyclazocine, cyclazodone, cyclexanone, cyclindole, cycliramine, cyclizine, cyclobarbital, cyclobendazole, cyclobenzaprine, cyclobutoic acid, cyclobutyrol, cyclocumarol, cyclofenil, cycloguanil, cycloheximide, cyclomenol, cyclomethycaine, cyclopentamine, cyclopenthiazide, cyclopentolate, cyclophenazine, cyclophosphamide, cyclopregnol, cyclopyrronium, cycloserine, cyclothiazide, cyclovalone, cyclotiamine, cycrimine, cyfluthrin, cyhalothrin, cyheptamide, cyheptropine, cynarine, cypenamine, cypermethrin, cypothrin, cyprazepam, cyprenorphine, cyprodenate, cyproheptadine, cyprolidol, cyproquinate, cyproterone, cyproximide, cyromazine, cysteamine, cysteine, cystine, cytarabine, cythiolate, dabelotine, dabigatran, dabuzalgron, dacarbazine, dacemazine, dacinostat, dacisteine, dacopafant, dactinomycin, dacuronium, dagapamil, dagluril, dalbavancin, dalbraminol, dalcotidine, daledalin, dalfopristin, dalteparin, daltroban, dalvastatin, dametralast, damotepine, danazol, daniquidone, danittracen, danofloxacin, danosteine, danthron, dantrolene, dapiprazole, dapitant, dapivirine, dapoxetine, dapsone, daptomycin, darbufelone, darenzepine, darglitazone, darifenacin, darodipine, darunavir, darusentan, dasantafil, dateliptium, daunorubicin, daxalipram, dazadrol, dazepinil, dazidamine, dazmegrel, dazolicine, dazopride, dazoquinast, dazoxiben, deboxament, debrisoquin, decamethonium, decimemide, decitabine, decitropine, declenperone, declopramide, decloxizine, decominol, decoquinate, dectaflur, deditonium, deferasirox, deferiprone, deferoxamine, deflazacort, defosfamine, defoslimod, degarelix, dehydroacetic acid, dehydrocholic acid, dehydroemetine, delanterone, delapril, delavirdine, delquamine, deergotrile, delfantrine, delfaprazine, selmadinone, delmetacin, delmpinol, delorazepam, deloxolone, delprostenate, delucemine, dembrexine, demecarium, demeclocycline, demecolcine, demecycline, demegestone, demelverine, demexiptiline, democonazole, demoxepam, demoxytocin, denatonium, denaverine, denbufylline, denipride, denofungin, denopamine, denotivir, denpidazone, denufosol, denzimol, depelestat, depramine, depreotide, deprodone, deprostil, deptropine, dequalinium, deracoxib, deramciclane, derigidole, derpanicaine, dersalazine, desapidin, desciclovir, descinolone, deserpidine, desipramine, deeslanoside, desloratidine, deslorelin, desmeninol, desmethylmoramide, desmopressin, desocriptine, desogestrel, desmorphine, desonide, desoximetasone, desoxycorticosterone, desvenlafaxine, detajmium, detanosal, deterenol, detirelix, deticiclovir, detromidine, detorubicin, detrothyronine, devapamil, devazepide, dexamethasone, dexamisole, dexbrompheniramine, dexbudesonide, dexchlorpheniramine, dexclamol, dexecadotril, dexefaroxan, dexetimide, dexetozoline, dexfenfluramine, dexfosfoserine, dexibuprofen, deximafen, dexindoprofen, dexivacaine, dexketoprofen, dexlofexidine, dexloxiglumide, dexmedetomidine, dexmethylphenidate, dexnafenodonee, dexniguldipine, dexnorgestrel, dexormaplatin, dexoxadrol, dexpanthenol, dexpemedolac, dexpropranolol, dexproxibutene, dexrazoxane, dexsecoverine, dexsotalol, dextilidine, dextiopronin, dextofisopam, dextroamphetamine, dextrofemine, dextromethorphan, dextromoramide, dextrorphan, dextrothyroxine, dexcerapimil, sezaguanine, dezinamide, dezocine, diacerein, diacetamate, diacetolol, diamfenetide, diamocaine, diampromide, diamthiazole, diapamide, diarbarone, diathymosulfone, diatrizoate, diaveridine, diazepam, diaziquone, diazoxide, dibekacin, dibemethine, dibenzepin, dibenzothiophene, dibrompropamidine, bibromsalan, dibrospidium, dibucaine, dibuprol, dibupyrone, dibusadol, dicarbine, dicarfen, dichloralphenazone, dichloramine, dichlorisone, dichlormezanone, dichlorophen, dichlorphenarsine, dichloroxylenol, dichlorphenamide, dichlovos, diciferron, dicirenone, diclazuril, diclofenac, diclofenamide, diclofensine, diclofutrime, diclometide, diclonixin, dicloralurea, dicloxacillin, dicloinium, dicummol, dicyclomine, didanosine, didrovaltrate, dieldrin, dienestrol, dienogest, diethadione, diethylphthalate, diethylcarbamazine, dietylpropion, diethylstilbestrol, dethylthambutene, dietyltoluamide, dietifen, difebarbamate, difemerine, difemetorex, difenamizole, difencloxazine, difenoximide, difenoxin, difetarsone, difeterol, diflomotecan, diflorasone, difloxacin, difluanine, diflucortolone, diflumidone, diflunisal, difluprednate, diftalone, digitalis, digitoxin, digoxin, dihexyverine, dihydralazine, dihydrocodeine, dihydroergotamine, dihydrostreptomycin, dihydrotachysterol, diisobutylaminobenzoyloxypropyl theophylline, diisopromine, diisopropanolamine, diisopropylamine, dilazep, dilevalol, dilmefone, diloxanide, diltiazem, dimabefylline, dimadectin, dimecamine, dimeclonium, dimecrotic acid, dimefadane, dimefline, dimelazine, dimenhydrinate, dimenoxadol, dimepheptanol, dimepranol, dimepregnen, dimepropion, dimeprozan, dimesna, dimesone, dimetacrine, dimetamfetamine, dimethadione, dimethazan, dimethisoquin, dimethisterone, dimetholizine, dimethothizine, dimethoxanate, dimethylaminoethyl reserpilinate, dimethylthambutene, dimethyltubocurarinium, dimetipirium, dimetofrine, dimetridazole, diminazene, dimiracetam, dimoxamine, dimoxaprost, dimoxyline, dimpylate, dinaline, dinazafone, diniprofylline, dinitolmide, dinoprost, dinoprostone, dinsed, diohippuric acid, diosmin, diotyrosine, dioxadrol, dioxamate, dioxaphetyl butyrate, dioxation, dioxethedrin, dioxifedrine, dioxybenazone, dioxyline, dipenine, diperodon, diphemanil, diphenadione, diphenan, diphenchloxazine, diphenhydramine, diphenidol, diphenoxylate, diphenylpiperidinomethyldioxolan, diphenylpyraline, diphenoxazide, dipipanone, dipiproverine, dipivefrin, diprafenone, diprenorphine, diprobutine, diprofene, diprogulic acid, diproleandomycin, diprofylline, diproqualone, diproteverine, diprotrizoate, diproxadol, dipyridamole, dipyrithione, dipyrocetyl, dipyrone, diquafosol, dirithomycin, dirlotapide, disermolide, disquonium, disobutamide, sidofenin, disogluside, disopyramide, disoxaril, distigmine, disufenton, disulergine, disulfamide, disulfuram, disuprazoole, ditazole, ditekiren, ditercalinium, dithiaanine, ditiocade, ditiocarb, ditiomustane, ditolamide, ditophal, divabuterol, divalproex, divaplon, dixanthogen, dizatrifone, dizcilpine, dobesilate, dobupride, dobutamide, dobutamine, docarpamine, docebenone, docetaxel, doconazole, doconexent, docosanol, docusate, dodeclonium, dodicin, dofamium, dofequidar, dofetilide, dolasetron, doliracetam, domazoline, domiodol, domiphen, domipizone, domitroban, domoprednate, domoxin, domperidone, donepezil, donetidine, donitriptan, dopamantine, dopamine, dopexamine, dopropidil, doqualast, dorampimod, doramectin, doranidazole, dorastine, soreptidei, doretinel, doripenem, dorzolamide. dosergoside, dosmalfate, dotarizine, dotefonium, dothiepin, doxacurium, doxapram, doxaprost, doxazosin, doxefazepam, doxenitoin, doxepine, doxergocalciferol, doxibetasol, doxifluridine, doxofylline, doxorubicin, doxpicomine, doxycycline, doxylamine, drafiazine, dramedilol, draquinolo, drazidox, dribendazolew, drimidene, drobuline, drocinonide, droclidinium, drofenine, droloxifene, drometrizole, dromostanolone, dronabinol, drinedarone, dropempine, droperidol, droprenilamine, dropropizine, drospirenone, drotaverine, drotebanol, droxacin, droxicamide, droxicam, droxidopa, droxinavir, droxypropine, duazomycin, dulofibrate, duloxetine, dulozafone, dumorelin, dumetacin, duoperone, dupracetam, dutasteride, dyclonine, dyhydrogestrone, dymanthine, dyphylline, ebalzotan, ebastine, eberconazole, ebiratide, ebrotidine, ebselen, ecabapide, ecabet, ecadotril, ecalcidene, ecamsule, ecastolol, ecenofloxacin, echothiophate, ecipramidil, eclanamine, eclazolast, ecomustine, econazole, ecopipam, ecraprost, ectylurea, edaglitazone, edaravone, edatrexate, edelfosine, edetol, edifolone, edogestrone, edonentan, edotecarin, edotreotide, edoxudine, edratide, edronocaine, edrophonium, efaproxiral, efaroxan, efavirenz, efegatran, efepristin, efetozole, efletirizine, eflornithine, efloxate, eflucimibe, elfumast, efonidipine, efrotomycin, eganoprost, eglumetad, egtazic acid, equalen, elacridar, elantrine, elanzepine, elaarofiban, elbanizine, eldacimibe, eletriptan, elfazepam, elgotipine, elinafide, eliprodil, elisartan, ellagic acid, elliptinium, elmustine, elnadipine, elopiprazole, elsamitrucin, eltanolone, eltenac, eltoprazine, elucaine, elvucitabine, elzasonan, elziverine, emakalim, emapunil, embramine, embusartan, embutramide, emedastine, emepronium, emetine, emeglitate, emilium, emiteflur, emiverine, emodepside, emopamil, emorfazone, emtricitabine, emylcamate, enadoline, enalapril, enalaprilat, enalkiren, enazadrem, enbucrilate, encamide, enciprazine, enclomiphene, encyprate, endixaprine, endomide, endralazine, endrysone, enecadin, enefexine, enestebol, enfenamic acid, enfluvirtide, englitazone, eniclobrate, enilconazole, enilospirone, eniluracil, eniporide, enisoprost, enloplatin, enocitabine, enofelast, enolicam, enoxacin, enoxamast, enoxaparin, enoximone, enoxolone, enipiprazole, enpiroline, enprazepine, enprofylline, enpromate, enprostil, enramycin, enrasentan, enrofloxacin, ensacillin, ensulizole, entacapone, entecavir, entsulfon, enviomycin, enviradene, enviroxime, enzacamene, anzastaurin, epalrestat, epanolol, eperezolid, eperisone, epervudine, ephedrine, epicamide, epicillin, epicriptine, epiestriol, epimestrol, epinastine, epinephrine, epinepheryl, epipropidine, epirizole, apiroprim, epirubicin, epitetracycline, epithiazide, epitiostanol, eplerenone, elivanserin, epoprostenol, epostane, eprazinone, eprinomectin, epristeride, eprobemide, eprosartan, eprovafen, eproxindine, eprozinol, epsipranel, epaloprost, eptapirone, eptaplatin, eptastigmine, eptazocin, eptifibatide, equillin, erbulozole, erdosteine, ergo calciferol, ergonovine, ergotamine, eritoran, erizepine, erlotinib, ercamide, ersentilide, ertapenem, ertiprotafib, erythrity tetranitrate, erythromycin, esafloxacin, esaprazole, esatenolol, escitalopram, esculamine, eseridine, esflurbiprofen, esketamine, escarbazepine, esmolol, esomeprazole, esonarimod, esorubicin, esoxybutynin, espatropate, esproquin, estazolam, estradiol, estramustine, estrazinol, estriol, estrofurate, estrone, estropipaten esupone, eszopclone, etabenzarone, etacepride, etafedrine, etafenone, etalocib, etamestrol, etaminile, etamiphylline, etamocycline, etanidazole, etanterol, etaqualone, etarotene, etasuline, etazepine, etazolate, etebenecid, eterobarb, etersalate, ethacridine, ethacrynic acid, ehtambutol, ethamivan, ethamsylate, ethaverine, ethenzameide, ethiazide, ethinamate, ethinyl estradiol, ethionamide, ethisterone, ethoheptazine, ethomoxane, ethonam, ethopabate, ethopropazine, ethosuximide, ethotoin, ethoxazene, ethoxazorutoside, ethoxzolamide, ethybenztropine, ethyl biscoumacetate, ethyl carfluzepate, ethyl cartrizoate, ethyl dibunate, ethyl dirazepate, ethyl loflazepate, ethylestrenol, ethylhydrocupreine, ethylmethylthiambutene, ethylmorphine, ethylnorepinepherine, ethylstilbamine, ethylnerone, ethylnodil, ethypicone, etibendazole, eticlopride, eticyclidine, etidocaine, etidronate, etidronic acid, etifelmine, etifenin, etifoxine, etilamfetamine, etilefrine, etilevodopa, etinidine, etipirium, etiprendol, etiproston, etiracetam, etiroxate, etisazole, etisomicin, etisulergine, etizolam, etocarlide, etocrylene, etodolac, etodroxizine, etofamide, etofenamate, etofenprox, etofibrate, etofermin, etofuradine, etofylline, etoglucid, eorolex, etolotifen, etoloxamine, etomidate, etomidoline, etomoxir, etomitazene, etonogestrel, etoperidone, etoposide, etoprindole, etoprine, etoricoxib, etorphine, etosalamide, etoxadrol, etoxeridine, etozolin, etrabamine, etravirine, etretinate, etriciguat, etryptamine, etymemazine, eucaine, eucalyptol, eugenol, euprocin, evandamine, evernimicin, everolimus, evicromil, exalamide, exametazime, examorelin, exaprolol, exatecan, exemestane, exepanol, exifone, exiprofen, exisulind, ezetimibe, ezlopitant, fadolmidine, fadrozole, falecalcitriol, falintolol, falipamil, falnidamol, famciclovir, famirapinium, famotidine, famotine, fampridine, famprofazone, fampronil, fananserin, fanapanel, fandofloxacin, fandosentan, fanetizole, fantofarone, fantridone, farglitazar, fasidotril, fasiplon, fasoracetam, faudil, fazadinium, fazarabine, febantel, febarbamate, febuprol, febuverine, febuxostat, feclemine, feclobuzone, fedotozine, fedrilate, felbamate, felbinac, felipyrine, felodipine, feloprentan, felypressin, femoxetine, fenabutene, fenacetinol, fenaclon, fenadiazole, fenaftic acid, fenalamide, femalcomine, fenamifuril, fenamole, fenaperone, fenbendazole, fenbenicillin, fenbufen, fenbutreazate, fencamfamin, fencibutirol, fenclexonium, fleclofenac, fenclonine, fenclorac, fenclozic acid, fendiline, fendizoate, fendosal, feneritrol, fenestrel, fenethazine, fenethylline, fenetradil, fenfiumizole, fenfluramine, flenfluthrin, fengabine, fenharmane, fenimide, feniodium, fenipentol, fenirfibrate, fenisorex, fenitrothion, fenleuton, fenmetozole, fenmetraminde, fenobam, fenocinol, fenocitimine, fenofibrate, fenoldopam, fenoprofen, fenoterol, fenoerine, fenoxazoline, fenoxedil, fenozolone, fenpentadiol, fenperate, fenprpalone, fenpipramide, fenpiprane, fenpiverinium, fenprinast, fenproporex, fenprostalene, fenquiaone, fenretinide, fenspiride, fentanyl, fenthion, fentiazac, fenticlor, fenticonazolem, fentonium, fenvalerate, fenyripol, fepentolic acid, fepitrizol, fepradinol, feprazone, fepromide, feprosidnine, ferpifosate, fesoterodine, fetoxylate, fexicaine, fexinidazole, fexofenadine, fezatione, fezolamine, fiacitabine, fialuridine, fibracillin, fidarestat, fidexaban, fiduxosin, figopitant, filaminast, filenadol, filipin, finafloxacin, finasteride, fingolimod, fipamezole, fipexide, fipronil, firocoxib, flavamine, flavodic acid, flavodilol, flavoxate, flazalone, flecamide, flerobuterol, fleroxacin, flesinoxan, flestolol, fletazepam, flezelastine, flibanserin, flindokalner, flocalcitriol, floctafenine, flomoxef, floptopione, florantyrone, flordipine, floredil, florfenicol, florifenine, flosatidil, flosequinan, flosulide, flotrenizine, floverine, floxacillin, floxacrine, floxuridine, flucizine, flualamine, fluanisone, fluazacort, fluazuron, flubanilate, flubendazole, flubepride, flucarbril, flucetorex, flucindole, flucinprazine, flucloronide, fluconazole, flucrylate, flucytosine, fludalanine, fludarabine, fludazonium, fludeoxyglucose, fludiazepam, fludorex, fludoxopone, fludrocortisone, flufenamic acid, flufenisal, flufosal, flufylline, flugestone, fluindarol, fluindione, flumazenil, flimecinol, flumedroxone, flumequine, flumeridone, flumethasone, flumethiazole, flumetramide, flumexadol, flumezapine, fluminorex, flumizole, flumoxonide, flunamine, flunarizine, flunidazole, flunisolide, flunitrazepam, flunixin, flunoprost, flunoxaprofen, fluocinolone, fluocinonide, fluocortin butyl, fluocortolone, fluorescein, fluoresone, fluorodopa, fluorometholone, fluorosalan, fluorouracil, fluotracen, fluoxetine, fluoxymesterone, fluparoxan, flupentixol, fluperamide, fluperlapine, fluperolone, flupheazine, flupimazine, flupirtine, flupranone, fluprazine, fluprednidene, fluprednisolone, fluprofen, fluprofylline, fluproquazone, fluprostenol, fluquazone, fluradoline, flurandrenolide, flurantel, flurazepam, flurbiprofen, fluretofen, flurithromycin, fluorocitabine, fluorofamide, fluorogestone, flusoxolol, fluspiperone, fluspirilene, flutamide, flutazolam, flutemazepam, flutiazin, fluticasone, flutizenol, flutomidate, flutonidine, flutoprazepam, flutrimazole, flutroline, flutropium, fluvastatin, fluvoxamine, fluzinamide, fluzoperine, fodipir, folic acid, fomepizole, fomidacillin, fominoben, fomiversen, fomocaine, fonazine, fondaparinux, fopirtoline, forasartan, forfenimex, forebolone, formestane, formetorex, forminitrazole, formocortal, formoterol, forodesine, foropafant, fosamprenavir, fosarilate, fosazepam, fosenazide, fosfluconazole, fosfocreatinine, fosfomycin, fosfonet, fosfosal, fosfructose, fosinopril, fosinoprilat, fosmenic acid, fosmidomycin, fosopamine, fosphenyloin, fospirate, fosquidone, fostedil, fosrtriecin, fosveset, fotemustine, fortrenamine, fozivudine, frabuprofen, fradafiban, frakefamide, framycetin, frentizole, freselestat, fronepidil, fropenem, frovatriptan, froxiprost, ftaxilide, ftivazide, ftormetazine, ftorpropazine, fubrogonium, fudosteine, fuladectin, fulvestrant, fumagillin, fumoxicillin, fungimycin, fuprazole, furacrinic acid, furafylline, furalazine, furaltadone, furaprofen, furazabol, furazolidone, furazolium, furbicillin, furcloprofen, furegrelate, furethidine, furfenorex, furidarone, furmethoxadone, fumidipine, furobufen, furodazole, furofenac, furomazine, furomine, furosemide, furostilbestrol, fursalan, fursultiamine, furtherene, furtrethonium, fusafungine, fusidate, fusidic acid, fuzlocillin, gabapentin, gabapexate, gaboxadol, gacyclidine, gadobenate, gadobutrol, gadocolectic acid, gadodiamine, gadofosveset, gadomelitol, gadopenamide, gadopentetate, gadoteric acid, gadoteridol, gadoversetamide, gadoxetate, gadoxeticaicid, galamustine, galantamine, galarubicin, galasomite, galdansetron, gallamine triethiodide, gallopamil, galocitabine, galosemide, galtifenin, gamfexine, gamolenic acid, gamaxolone, ganciclovir, ganefromycin, ganglefene, ganstigmine, gantacurium, gantofiban, gapicomine, gapromidine, garenoxacin, gatifloxacin, gavestinel, geclosporin, gedocamil, gefarnate, gefitinib, gemazocine, gemcabene, gemcadiol, gemcitabine, gemeprost, genfibrozil, gemifloxacin, gemopatrilat, gentamicin, gepefrine, gepirone, geroquinol, gestaclone, gestadienol, gestodene, gestonorone, gestrinone, gevotroline, gimatecan, gimeracil, giparmen, giracodazole, giractide, girisopam, gitaloxin, gitoformate, glafenine, glaspimod, glatiramer acetate, glemanserin, glenvastatin, gliamilide, glibotnuride, glibutimine, glicaramide, glicetanide, gliclazide, glicondamine, glidazamide, glifiumide, glimepiride, glipalamide, glipizide, gliquidone, glisamuride, glisentide, glisindamine, glisolamide, glisoxepide, gloxazone, gloximonam, glucametacin, glucosamine, gluronolactone, glucuronamide, glunicate, glyburide, glybuthiazole, glubuzole, gycopyrrolate, glycylamide, glyhexamide, glymidine, glyoctamide, glyparamide, glypinamide, glyprothiazole, glysobuzole, goralatide, goserelin, gramicidin, granisetron, grepafloxacin, griseofulvin, guabenxan, guacetisal, guafecainol, guaiactamine, guaiapate, guaietolin, guaifenesin, guaimesal, guaisteine, guaithylline, guanabenz, guanacline, guanadrel, guanazodine, guanclofine, guancydine, guanethidine, guanfacine, guanisoquin, guanoclor, guanoctine, guanoxabenz, guanoxan, guanoxyfen, gusperimus, halazepam, halazone, halcinonide, halethazole, halobetasol, halocortolone, halofantrine, halofenate, halofuginone, halometasone, halonamine, halopemide, halopenium, haloperidol, halopredone, haloprogesterone, haloprogin, haloxazolam, haloxon, haloqionol, hamycin, hedaquinium, heliomycin, hepronicate, heptabarbital, heptaverine, heptolamide, hepzidine, heroin, hetacillin, hetaflur, heteronium, hexachlorophene, hexacyclonate, hexacyprone, hexadiline, hexafluorenium, hexamethonium, hexaminolevulinate, hexapradol, hexaprofen, hexapropymate, hexasonium, hexazole, hexedine, hexestrol, hexetidine, hexobarbital, hexobendine, hexocyclium, hexoprenaline, hexopyrronium, heylcaine, histamine, histapyrrodine, histidine, homarylamine, homatropine, homidium, homochlorcyclizine, homofenazine, homopipramol, homosalate, homprenorphine, hopantenic acid, hoquizil, hycanthone, hydracarbazine, hydralazine, hydragaphen, hydrobentizide, hydrochlorothiazide, hydrocodone, hydrocortisone, hydroflumethiazide, hydromadinone, hydromorphinol, hydromorphone, hydroquinone, hydroxyindasate, hydroxyindasol, hydro xocobalamin, hydroxyamphetamine, hydroxychloroquin, hydroxydione, hydroxypethidine, hydroxyphenamate, hydroxyprocaine, hydroxyprogesterone, hydroxypyridine tartrate, hydroxystenozole, hydroxystilbamidine, hydroxytetracaine, hydroxyzine, hymecromone, hyoscyamine, ibafloxacin, ibandronate, ibazocine, ibopamine, ibrolipim, ibrotamide, ibudalast, ibufenac, ibuprofen, ibuproxam, ibutamoren, ibuterol, ibutilide, ibuverine, icaridin, icatibant, iclaprim, icazepam, icodulinium, icofungipen, ifometasone, icopezil, icosapent, icospiramide, icotidine, icrocaptide, idarubicin, idaverine, idazoxan, idebenone, idenast, idoxifene, idoxuridine, idralfidine, idramantone, idraparinux, idrapril, idremcinal, idrociliamide, idronoxil, idropranolol, iferanserin, ifetroban, ifosfamide, ifoxetine, iganidipine, igmesine, iguratimod, ilaprazole, ilatreotide, ilepcimide, iliparcil, ilmofosine, iloomastat, ilonidap, iloperidone, imafen, imanixil, imatinib, imazodan, imcarbofos, imiclopazine, imidafenacin, imidapril, imidaprilat, imidocarb, imidoline, imidurea, imiglitazar, imiloxan, iminophenimide, imipenem, imipramine, imipraminoxide, imiquimod, imirestat, imitrodast, imolamine, imoxiterol, impacarzine, implitapide, impromidine, improsulfan, imuracetam, inamirone, inaperisone, incadronic acid, indacaterol, indacrinone, indalpine, indanazoline, indanidine, indanorex, indapamide, indatraline, indecamide, indeloxazine, indenolol, indibulin, indigotindisulfonate, indinavir, indiplon, indisetron, indobufen, indocate, indocyanine green, indolapril, indolidan, indomethacin, indopanolol, indopine, indoprofen, indoramin, indorenate, indoxole, indriline, inecalcitol, ingliforib, inicarone, inocterone acetate, inogatran, inosine, inositol, improquoone, intoplicine, intrazole, intriptyline, inulin, iobenguane, iobenzamic acid, iobitridol, iobutoic acid, icanlidic acid, iocarmic acid, iocetamic acid, iodamine, iodipamide, iodixanol, iodoantipyrine, iodocholesterol, iodohippurate, iodoquinol, iodothiouracil, idoxamic acid, iofetamine, ioflupane, iofratol, ioglicic acid, ioglucol, ioglunide, ioglycamic acid, iogulaamide, iohexyl, iolidonic acid, iolixanic acid, iolopride, iomazenil, iomeglamic acid, iomeprol, iomethin, iometopane, iomorinic acid, iopamidol, iopanoic acid, iopentol, iophendylate, iophenoxic acid, iopromide, iopronic acid, iopydol, iopydone, iosarcol, isofenamic acid, ioseric acid, iosimenol, iosimide, iosulamide, iosumetic acid, iotasul, ioteric acid, iothalamate, iothalamic acid, iotranic acid, iotriside, iotrizoic acid, iotrolan, iotroxic acid, iotyrosine, iovesol, ioxabrolic acid, ioxaglic acid, ioxilan, ioxitalamic acid, ioxotrizoic acid, iozomic acid, ipamorelin, ipazilide, ipenoxazone, ipexidine, ipidacrine, ipodate, iprgratine, ipramidil, ipratropium, ipravacaine, iprazochrome, ipriflavone, iprindole, ipocinidine, iproclozide, iprocrodol, iprofenin, iproheptine, iproniazide, ipronidazole, iproplatin, iprotiazem, iproxamine, iprozilamine, ipsalazide, ipsapirone, iquindamine, iralukast, irampanel, irbesartan, irindalone, irinotecan, irloxacin, irofulven, irolapride, iroxanadine, irsogladine, irtemazole, isalidole, isalsteine, isamfazone, isamoltan, isamoxole, isatoribine, isaxonine, isbogrel, isbufylline, ispamicin, isoamilinile, isobromindione, isobucaine, isobutamben, isocarboxazid, isoconazole, isocromil, isoetharine, isofiupredone, isofluorophate, isomazole, isomerol, isometamidium, isomethadone, isometheptene, isomolpan, isoamylamine, isoniazid, isonixin, isoprazole, isoprednidene, isoprofen, isopropamide, isopropicillin, isoproterenol, isosrbide, isospaglumic acid, isosulfan blue, isosulpride, isothipendyl, isotiquimide, isotretinoin, isoxaprolol, isoxepac, isoxicam, isoxsuprine, isradipine, israpafant, istrdefylline, itameline, itanoxone, itasetron, itazigrel, itopride, itraconazole, itriglumide, itrocamide, itrocinonide, iturelix, ivbradine, ivarimod, ivermectin, ivoqualine, ixabepilone, izonsteride, josamycin, kainic acid, kalafungin, kanamycin, kebuzone, keracyanin, ketamine, ketanserin, ketazocine, ketazolam, kethoxal, ketipramine, ketobemidone, ketocaine, ketocainol, ketoconazole, ketoprofen, ketorfanol, ketorolac, ketotifen, ketotrexate, khellin, khelloside, kitasamycin, labetalol, labradimil, lachesine, lacidipine, lacosamide, lactalfate, lactilol, lactulose, ladirubicin, ladostigil, laflunimus, lafutiine, laidlomycin propionate, lamifiban, lamivudine, lamotrigine, lamitidine, lanatoside, landiolol, lanepitant, lanicemine, laniquidar, lanoconazole, lanperisone, lanproston, lanreotide, lansoprazole, lapatinib, lapisteride, laprafylline, lapyrium, laquinimod, lasalocid, lasinavir, lasofoxifene, latanoprost, laudexium, laurcetium, laurocapram, lauroguadine, laurolinium, lauryl isoquinolinium, lavoltidine, lazabemide, lecimibide, ledazerol, ledoxantrone, lefetamine, leflunomide, lefradafiban, leiopyrrole, lemidosul, lemidipine, leminoprazole, lemoxinol, lemuteporfin, lanalidomine, lenampicillin, lenapenem, leniquisin, leuperone, leptacline, lercanidipine, lergotrile, lerisetron, lesoptiron, lestaurtinib, leteprinim, leteprinim, letimide, letosteine, letrazuril, letrozole, leucinocaine, leucocianidol, leucovorin, leurubicin, levalbuterol, levallorphan, levamfetamine, levamisole, levcromakalim, levcycloserine, levdobutamine, levemoamil, levetiracetam, levisoprenaline, levlofexidine, levmetamfetamine, levobetaxolol, levobunolol, levobupiacaine, levocabastine, levocamitine, levodopa, levodropizine, levofacetoperane, levofenfluramine, levofloxacin, levofluraltadone, levoleucovorin, levomenol, levomepromazine, levomethadone, levomethadyl acetate, levomethorphan, levometiomeprazine, levomoprolol, levomoramide, levonantradol, levonordefrin, levonorgestrel, levophenacylmorphan, levopropoxyphene, levopropylcilline, levopropuylhexedrine, levoprotiline, levorin, levormeloxifene, levorphanol, levosalbutamol, levosemotiadil, levosimendan, levosulpiride, levothyroxine, levotofisopam, levoxadrol, lexipafant, lexithromycin, lexofenac, liarozole, libecillide, libenzapril, licarbazepine, licofelone, licostinel, lidadronic acid, lidamine, lidanserin, lidocaine, lidoferin, lidorestat, lifariaine, lifibrate, lifibrol, lilopristone, limaprost, limazocic acid, linarotene, lincomycin, lindane, linetastine, linezolid, linogliride, linopirdine, linotroban, lisinidomine, lintitript, lintopride, liothyronine, lipoic acid, liraglutide, liranaftate, lirequinil, lirexapride, lirimilast, liroldine, lisadimate, lisinopril, lisofylline, lisuride, litomeglovir, litoxetine, litracen, lividomycin, lixazinone, lixivaptan, lobapolatin, lobeline, lobendazole, lobenzarit, lobucavir, lobuprofen, locicortolone, lodaxaprine, lodazecar, lodelaben, lodenosine, lodinixil, lodiperone, lodoxamide, lofemizole, lofendazam, lofentanil, lofepramine, lofexidine, loflucarban, lombazole, lomefloxacin, lomeguarib, lomerizine, lometraline, lometrexol, lomevactone, lomifylline, lomofungin, lomustine, lonafarnib, lonapalene, lonaprofen, lonazolac, lonidamine, loperamide, lopinavir, lopirazepam, lopobutan, loprazolam, loracarbef, lorajmine, lorapride, lorazepam, lorbamate, lorcamide, lorcinadol, loreclezole, lorglumide, lormetazepam, lornoxicam, lopiprazole, lortalamine, lorzafone, losartan, losigamone, losindole, losmiprofen, losoxantrone, losulazine, loteprednol, lotrafiban, lotrifen, lotucaine, lovastatin, loviride, loxanast, loxapine, loxiglumide, loxoprofen, loxoribine, lozilurea, lubazodone, lubeluzole, lubiprostone, lucanthone, lucartamide, lucimycin, lufenuron, lufironil, lufuradom, luliconazole, lumiracoxib, lupitidine, luprostiol, lurasidone, lurosetron, lurototecan, lusaperidone, luxabendazole, lydimycin, lymecycline, lynestrenol, lypressin, mabuprofen, mabuterol, maduramicin, mafenide, mafoprazine, mafosfamide, malathion, maleylsulfathiazole, malotilate, mangafodipir, manidipine, manifaxine, mannomustine, manozodil, mantabegron, mapinastine, maprotiline, maraviroc, marbofloxacin, maribavir, maridomycin, marimastat, mariptiline, maropitant, maroxepin, masoprocol, maxacalcitol, maytansine, mazapertine, mazaticol, mazindol, maziperidone, mazokalim, mebanazine, mebendazole, menbenoside, mebeverine, mebezonium, mebhydrolin, mebiquine, mebolazine, mebrofenin, mebutamate, mebutizide, mecamylamine, mecarbinate, mecetronium, meciadanil, mecinarone, meclinertant, meclizine, meclocycline, meclofenamaic acid, meclofenoxate, meclonazepam, mecloqualone, meclorisone dibutyrate, mecloxamine, mecobalamin, medazepam, medazomide, medetomidine, medibazine, medifoxamine, medorinone, medorubicin, medrogestone, medronic acid, medroxalol, medroxyprogesterone acetate, medrylamine, medrysone, mefeclorazine, mefenamic acid, mefenidil, mefenidramium, mefenorex, mefeserpine, mefexamide, mefloquine, mefruside, megalomyciin, megestrol, megace, meglitinide, meglucycline, meglumine, meglutol, meladrizine, melagatran, melarsomine, melarsonyl, melarsoprol, meldonium, melengestrol acetate, meletimide, melevodopa, melinamide, melitracen, melizame, meloxicam, melperone, melphalan, melquinast, meluadrine, mamantine, memotine, menabitan, menadiol, menadione, menadoxime, menatetrenone, menbutone, menfegol, menglytate, menitrazepam, menoctone, menogaril, menobentine, mepazine, mepenzolate, meperidine, mephenesin, mephenoxalone, mephentermine, mephenyloin, mephobarbital, mebaral, mepindolol, mepiperphenidol, mepiprazole, mepiroxol, mepitiostane, mepivacaine, mepixanox, mepramidil, meprednisone, meprobamate, meprochol, meproscillarin, meprotixol, meprylcaine, meptazinol, mequidox, mequinol, mequitamium, mequitazine, meradimqate, menthyl anthranilate, merafloxacin, meralein, meralluride, merbaphen, merbromin, mercaptomerin, mercaptopurine, mercuderamide, mercufenol, mercumatilin, mergocriptine, meribendan, merimepodib, meropenem, mersalyl, mertialide, mesabolone, mesalamine, meseclazone, mesocarb, mesoridazine, mesipiperone, mespirenone, mestanolone, mesterolone, mestranol, mesudipine, mesulergine, mesulfamide, mesulfen, mesuprine, metabromsalan, metbutethamine, metabutoxycaine, metacetamol, metaclazepam, metacresol, metaglycodol, metahexamide, metalkonium, metalol, metamelfalan, metamfazone, metamfenpramone, metampicillin, metanixin, metapramine, metaproterenol, metaraminol, metaxalone, metazamide, metazide, matazocine, metbufen, meteneprost, metergoline, metergotamine, metescufylline, metesculetol, metesind, metethoheptazine, metformin, methacholine, methacycline, methadone, methadyl acetate, methallenestril, methallibure, methalthiazide, methamphetamine, methandriol, methandrostenolone, methaniazide, methantheline, methaphenilene, methapyrilene, methaqualone, metharbital, methastyridone, methazolamide, methdilazine, methenamine, methenolone, metheptazine, methestrol, methetoin, methikcillin, methimazole, methiodal, methiomeprazine, methionine, methisazone, methitural, methixene, methocarbamol, methocidin, methohexital, methopholone, methoprene, methoserpidine, methotrexate, methotrimeprazine, methoxamine, methoxsalen, methoxyphedrine, methoxyphenamine, methoxypromazine, methscopolamine, methsuximide, methyclothiazide, methyl aminolevulinate, methyl palmoxirate, methyl salicylate, methylatropine, methylbenactyzium, methylbenzethonium, methylcromone, methyldesorphine, methyldihydromorphine, methyldopa, methylene blie, methylephedrine, methylergometrine, methylergonovine, methyllparaben, methylphenidate, methylprednisolone, methyltestosterone, methylthiouracil, methynodiol, methyprylon, methysergide, metiamide, metiapine, metiazinic acid, metibride, meticrane, metildigoxin, metindizate, metioprim, metioxate, metipirox, metiprenaline, metitepine, metizoline, metkephamid, metochalcone, metocinium, metoclopramide, metocurine, metofenazate, metogest, metolazone, metomidate, metopimazine, metopon, metoprine, metoprolol, metoquizine, metoserpate, metostilenol, metoxepin, metrafazoline, metralindole, metrazifone, metrenperone, metribolone, metrifonate, metrifudil, metrizamide, metrizoate, metronidiazole, meturedepa, metyrapone, metyrosine, mevastatin, mexafylline, mexazolam, mexenone, mexiletine, mexiprosil, mexoprofen, mexrenoate, mezacopride, mezepine, mezilamine, mezlocillin, miaanserin, mibefradil, mibolerone, miboplatin, micafungin, miconazole, micronomicin, midaflur, midafotel, midaglizole, midamaline, midaxifylline, midazogrel, midazolam, midecamycin, midestein, midodrine, midostaurin, mifentidine, mifepristone, mifobate, miglitol, miglustat, mikamycin, milacamide, milacemide, milameline, milataxel, milenperone, milfasartan, milipertine, miloxacin, milrinone, miltefosine, milverine, mimbane, minalrestat, minamestane, minaprine, minaxolone, mindodilol, mindoperone, minepentate, minocromil, minocycline, minodronic acid, minopafant, minoxidil, mioflaazine, mipitroban, mipragoside, miproxifene, mirfentanil, mirincamycin, miripirium, miriplatin, mirisetron, miristalkonium, miroprofen, mirosamicin, mirostipen, mirtazapine, misonidazole, misoprostol, mitemcinal, mitiglinide, mitindomine, mitobronitol, mitocarcin, mitoclomine, mitocromin, mitoflaxone, mitogillin, mitoguazone, mitolactol, mitomalcin, mitomycin, mitonafide, mitopodozide, mitoquidone, mitosper, mitolane, mitotenamine, mitoxantrone, mitozolomide, mitradipide, mivacurium, mivobulin, mivotilate, mixidine, mizolastine, mizoribine, mobecarb, mobenzoxamine, mocimycin, mociprazine, moclonemide, moctamide, modafinil, modaline, modecamide, modipafant, moexipril, moexiprilat, mofarotene, mofebtazone, mofegiline, mofezolac, mofloverine, mofoxine, mofuisteine, molfarnate, molinazone, molindone, molracetam, molsidomine, mometasone, monalazone, monatepil, monesin, monobenzone, monoctanoin, monometacrine, monophosphothiamine, monoxerutin, montelukast, monterelin, moperone, mopidamol, mopidralazine, moprolol, moquizone, morantel, morazone, morclofone, morforex, moricizine, morinamide, morniflumate, morocromen, moroxydine, morpheridine, morphine, morsuximide, mosapramine, mosapride, motapizone, motexafin, motrazepam, motrtinide, moveltipril, moxadolen, moxalactam, moxaprindine, moxastine, moxaverine, moxazocine, moxestrol, moxicoumone, moxidectin, moxifloxacin, moxilubant, moxipraquine, moxirapine, moxisylate, moxnidazole, moxonidine, mozavaptan, mozenavir, mubritnib, mupirocin, murabutide, muraglitazar, mureletecan, murocamide, muzolimine, mycophenolic acid, myfadol, myrophine, myrtecaine, nabazenil, nabilone, nabitan, naboctate, nabumetone, nacartocin, nadide, nadiofloxacin, nadolol, nadoxolol, nafagrel, nafamostat, nafarelin, nafazatrom, nafcaproic acid, nafcillin, nafenodone, nafenopin, nafetolol, nafimidone, nafiverine, naflocort, nafomine, nafoxadol, nafoxidine, nafronyl, naftalofos, naftazone, naftifine, naftopidil, naftoxate, naftypamide, naglivan, nalbuphine, nalfurafine, nalidixic acid, nalmefene, nalmexone, nalorphine, naloxone, naltrexone, naminidil, naminterol, namirotene, namoxyrate, nanafrocin, nandrolone, nanterinone, nantradol, napactadine, napamezole, naphazoline, naphthonone, napirimus, napitane, naproxime, naproxen, naproxol, napsagatran, naranol, narasin, naratriptan, nardetoterol, naroparcil, natamycin, nateglinide, navuridine, naxagolide, naxaprosteine, naxifylline, nealbarbital, nebantan, nebidrazine, nebivolol, neboglamine, nebracetam, nebramycin, necopidem, nedaplatin, nedocromil, nefazodone, nefiracetam, neflumozide, nefopam, nelarabine, neldazosin, nelezaprine, nelfinavir, neltenexine, nelzarabine, nemadectin, nemazoline, nemifitide, nemonapride, nemorubicin, neocinchophen, neomycin, neostigmine, nepadutant, nepafenac, nepaprazole, nepicastat, nepinalone, nequinate, neramexane, neraminol, nerbacadol, neridronic acid, nerisopam, nesapidil, nesiritide, nesosteine, nestifylline, neticonazole, netilmicin, netivudine, netobimin, netoglitazone, netupitant, neutramycin, neviparine, nexeridine, nexopamil, niacin, niacinamide, nialamide, niaprazine, nibroxane, nicafenine, nicainoprol, nicametane, nicanartine, nicaraven, nicarbazin, nicardipine, nicergoline, niceritol, niceverine, niclofolan, niclosamide, nicoboxil, nicoclonate, nicocodine, nicocortonide, nicocodidone, nicoduozide, nicofibrate, nicofuranose, nifurate, nicogrelate, nicomol, nicomorphine, nicopholine, nicoracetam, nicorandil, nicothiazone, nicotredole, nicoxamat, nictiazem, nictindole, nidroxyzone, nifedipine, nifekalant, nifenalol, nifenazone, niflumic acid, nifungin, nifiradene, nifuraldezone, nifuralide, nifuratel, nifuratrone, nifurdazil, nifurethazone, nifurfoline, nifurimide, nifurizone, nifurmazole, nifurmerone, nifuroquine, nifuroxazide, nifuroxime, nifurpipone, nifurpirinol, nifirprazine, nifurquinazol, nifursemizone, nifursol, nifurthiazole, nifurtimox, nifurtoinol, nifurvidine, nifurzide, nigludipine, nihydrazone, nikethamide, nileprost, nilprazole, niludipine, nilutamide, nilvadipine, nimazone, nimesulide, nimetazepam, nimidane, nimodipine, nimorazole, nimustane, neometacin, niperotidine, nipradilol, niprofazone, nitavoline, nirdazole, nisbuterol, nisobamate, nisoldipine, nisoxetine, nisterime, nitarsone, nitazoxanide, nitecapone, nithiamide, nitisinone, nitracrine, nitrafudan, nitralamine, nitramisole, nitraquazone, nitrazepam, nitrefazole, nitrendipine, nitrocefin, nitroclofene, nitrocycline, nitrodan, nitrofurantoin, nitrofurazone, nitromersol, nitromide, nitromifene, nitroscanate, nitrovin, nitroxinil, nitroxoline, nivazol, nivimedone, nizatidine, nizofenone, noberastine, nocloprost, nocodazole, nofecamide, nogalamycin, nolatrexed, nolinium, nolomirole, nolpitantium, nomegestrol, nomelidine, nomifensine, nonabine, nonaperone, nonapyrimine, nonathymulin, nonivamide, noracymethadol, norbolethone, norbudroine, norcholestenol, norclostebol, norcodeine, nordazepam, nordefrin, nordinone, norelgestromin, norepinephrine, norethandrolone, noethindrone, norethynodrel, noreximide, norfenefrine, norfloxacin, norgesterone, norgestimate, norgestomet, norgestrel, norgestrieneone, norletimol, norlevorphenol, normethadone, normorphine, norpipanone, nortetrazepam, nortopixantrone, nortriptyline, norvinisterone, nosantine, noscapine, nosiheptide, novobiocin, noxiptiline, noxytiolin, nuclomedone, nuclotixene, nufenoxole, nupafant, nuvenzepine, nylestriol, nylidrin, nystatin, obidoxime, ocaperidone, ocfentanil, ociltide, ocinaplon, octacaine, octafonium, octamoxin, octapinol, octatine, octaverine, octazamide, octenidine, octicizer, octimibate, octinoxate, octisalate, octocrylene, octodrine, octopamine, octotiamine, octreotide, octriptyline, octriazole, odalprofen, odapipam, odiparcil, ofloxacin, ofomine, oftasceine, oglufanide, olaflur, olamufloxacin, olanexidine, olanzapine, olaquindox, olcegepant, oleandomycin, oletimol, olmesartan, olopatadine, olpadronic acid, olpimedone, olprinone, olradipine, olsalazine, oltipraz, olvanil, omaciclovir, omapartrilat, omeprazole, omidoline, omigapil, omiloxetine, omoconazole, omonasteine, onapristone, ondansetron, ontazolast, ontianil, opanixil, opaviraline, opiniazide, opipramol, opratonium, orazamide, orazipone, orbofiban, orbutopril, orconazole, orientiparcin, oritavancin, orlistat, ormaplatin, ormeloxifene, ormetoprin, ornidazole, ornipreessin, ornithine, ornoprostil, orotic acid, orotirelin, orpanoxin, orphenadrine, ortataxel, orteteamine, osanetant, osaterone, oseltamivir, osemozotan, osmadizone, ospemifene, ostreogrycin, osutidine, otamixaban, otenzepad, oteracil, otilonium, otimerate, ouabain, oxabolon, oxabrexine, oxaceprol, oxacillin, oxadimedine, oxaflozane, oxaflumazine, oxagrelate, oxalinast, oxaliplatin, oxamarin, oxametacin, oxamisole, oxaminiquinem oxanamide, oxandrolone, oxantel, oxapadol, oxapium, oxaprazine, oxaprotiline, oxaprozin, oxcarbazole, oxatomide, oxazafone, oxazepam, oxazidone, oxazolam, oxazorone, oxcarbazepine, oxdralazine, oxeclosporin, oxedrine, oxeglitazar, oxeladin, oxendolone, oxepinac, oxetacillin, oxethazine, oxetorone, oxfendazole, oxfenicine, oxibendazole, oxibetaine, oxiconizole, oxidapamine, oxidronic acid, oxfentorex, oxifungin, oxigluttione, oxilofrine, oxilorphan, oximonam, oxindanac, oxiniacic acid, oxperomide, oxiracetam, oxiramide, oxisopred, oxisuran, oxitefonium, oxitriptan, oxitriptyline, oxtriponium, oxmetidine, oxodipine, oxogestone, oxolamine, oxolinic acid, oxomermazine, oxonazine, oxophenarsine, oxoprostol, oxpheneridine, oxprenoate, oxprenolol, oxtriphylline, oxbenzone, oxybutynin, oxychlorosene, oxycinchophen, oxyclipine, oxyclozanide, oxycodone, oxydipentonium, oxyfedrine, oxymesterone, oxymetazoline, oxymethalone, oxymorphone, oxypendyl, oxypertine, oxyphenbutazone, oxyphencyclimine, oxyphenisatin, oxyphenonium, oxypurinol, oxypurronium, oxyquinoline, oxyridazine, oxysonium, oxytetracycline, oxytocin, ozagrel, ozagamicin, ozolindone, paclitaxel, pacrindolol, pactimibe, padimate A, padimate Q, pafenolol, pagoclone, paldimycin, palinavir, paliperidone, palmidrol, palmoxirate, palonidipine, palonosertron, palosuran, pamabron, pamaqueside, pamaquin, pamicogrel, pamidronic acid, panadiplon, panamesine, pancopride, pancuronium, panipenem, panomifene, pantenicate, pantethine, panthenol, pantoprazole, panuramine, papverine, papveroline, parachlorphenol, parafiutizide, paramethadione, paramethasone acetate, paranitrosulfathiazole, paranyline, parapenzolate, parapropamol, pararosaniline, paraxazone, parbendazole, parcetasal, parconazole, parecoxib, pareptide, parethoxycaine, pargeverine, pargolol, pargyline, paricalcitol, paridocaine, parodilol, paromomycin, paroxetine, paroxypropione, parsalmide, particin, parvaquone, pasiniazid, pasireotide, patamostat, patupilone, paulomycin, paxamate, pazelliptine, pazinaclone, pazoxide, pazufloxacin, pecilocin, pecocycline, pefloxocin, pelanserin, peldesine, peliomycin, pelitinib, pelitrexol, pelretin, pelrinone, pelubiprofen, pemedolac, pemerid, pemetrexed, pemirolast, pemoline, penamecillin, penbutolol, penciclovir, pendecamine, pendetide, penfluridol, penflutizide, pengitoxin, penicillamine, penicillin G, penicillin V, penimepicycline, penimocycline, penirolol, penmesterol, penoctonium, penprostene, pentabamate, pentacynium, pentfluranol, pentagastrin, pentagestrone, pentalamide, pentamethonium, pentamidine, pentamorphone, pentamoxane, pentamustine, pentapiperide, pentapiperium, pentaquine, pentazocine, pentetic acid, pentreotide, penthienate, penthrichloral, pentiapine, pentifylline, pentigetide, pentisomicin, pentisomeide, pentizidone, pentobarbital, pentolinium, pentolonium, pentomone, pentopril, pentorex, pentosalen, pentostatin, pentoxifylline, pentoxyverine, pentrinitrol, pentylenetetrazol, peplomycin, pepstatin, peraclopone, peradoxime, perafensine, peralopride, peramivir, peraquisin, perastine, peratizole, perazine, perbufylline, perfomedil, perfosfamide, pegolide, perhexyline, periciazine, perifosine, perimetazine, perindopril, perindoprilat, perisoxal, perlapine, permethrin, perospirone, perphenazine, persilic acid, perzinfotel, petrichloral, pexantel, phanquone, phenacaine, phenacemide, phenacetin, phenactropinium, phenadoxone, phenaglycodol, phenamazoline, phenampromide, phenaphthazine, phenarsone, phenazocine, phenazopyridine, phenbutazone, phencarbamide, phencyclidine, phendimetrazine, phenelzine, pheneridine, phenethicillin, pheneturide, phenylglutarimide, phenicarbazide, phenindamine, phenindione, pheniprazine, pheniramine, phenisonone, phenmetrazine, phenobarbital, phenobutiodil, phenomorphan, phenothiazine, phenothrin, phenoxybenzamine, phenoxypropazine, phenprobamate, phenprocoumon, phenpromethamine, phensuximide, phentermine, phentolamine, phenyl aminosalicylic acid, phenylalanine, phenylbutazone, phenylephrine, phenylpropanolamine, phenylthiolone, phenyltoloxamine, phenyracillin, phenyramidol, phenyloin, pnetharbital, pholcodine, pholedrine, phoxim, phthalofyne, phthylsulfacetamide, phthalylsulfamethiazole, phthalylsulfathiazole, physostigmine. Phytic acid, phytonadione, pibaxizine, pibecarb, piberaline, piboserod, pibrozelesin, pibutidien, picafibrate, picartamide, picenadol, picilorex, piclamilast, piclonidine, piclopastine, picloxydine, picobenzide, picodralazine, picolamine, piconol, picoperine, picoplatin, picoprazole, picotamide, picotrin, picumast, picumeterol, pidobenzone, pidolacetamol, pidolicaicd, pidotimod, pifamine, pifinate, pifexole, piflutixol, piketoprofen, pildralazine, pilocarpine, pilsicamide, pimagedine, pimeclone, pimecrolimus, pimethylline, pimelautide, pimetacin, pimethixene, pimetine, imetremide, pimilprost, piminodine, pimobendan, pimonidazole, pimozide, pinacidil, pinadoline, pinafide, pinaverium, pinazepam, pincamide, pindolol, pinokalant, pinolcaine, pinoxepine, pioglitazone, pipacycline, pipamazine, pipamperone, pipazethate, pipebuzone, pipecuronium, pipemidicacid, pipendoxifene, pipenzolate, pipequaline, piperacetazine, piperacillin, piperamide, piperidolate, piperilate, piperocaine, piperonyl butoxide, piperoxan, piperphenidol, piperylone, pipobroman, pipoctanone, pipofezine, piposulfan, pipotiazine, pipoxizine, pipoxolan, pipradimadol, pipradrol, pipramadol, pipratecol, piprinhydrinate, pipocurarium, piprofurol, piprozolin, piquindone, piquizil, piracetam, pirandamine, pirarubicin, piraxelate, pirzmonam, pirazolac, pirbenicillin, pirbuterol, pirdonium, pirenoxine, pirenperone, pirezepine, pirepolol, piretanide, pirfenidone, pirbendil, piridicillin, piridocaine, piridoxilate, piridronic acid, pirifibrate, pirimiphos-ethyl, pirindazole, pirinixic acid, pirinixil, piriprost, piriqualone, pirisudanol, piritramide, piritrexin, pirlimycin, pirlindole, pirmagrel, pirmenol, pirnabine, piroctone, pirodavir, priodomast, pirogliride, piroheptine, pirolate, pirolazamide, piromidic acid, piroxantrone, piroxicam, piroxicillin, piroximone, pirozadil, pirprofen, pirquinozol, pirralkonium, pirsidomine, pirtenidine, pitenodil, pitofenone, pituxate, pivagabine, pivampicillin, pivenfrine, pivopril, pivoxazepam, pixantrone, pizotyline, plafbride, plaunotol, plauracin, pleconaril, pleuromulin, plevitrexed, plicamycin, plomestane, pobilukast, podilfen, podofilox, poldine, polymixin, polythiazide, pomisartan, ponalrestat, ponazuril, ponfibrate, porfiromycin, posaconazole, posatirelin, posizolid, poskine, practolol, pradolfoxacin, prajmalium, pralatrexate, pralidoxime, pralmorelin, pralnacasan, pramipexole, pramiracetam, pramoxine, prampine, pranazepide, pranidipine, prankulast, pranolium, pranoprofen, pranosal, prasterone, prasugrel, pratosartan, pravadoline, pravastatin, praxadine, prazarelix, prazepam, prazepine, praziquantel, prazitone, prazocillin, prazosin, preclamol, prednazate, prednazoline, prednicarbate, prednimustine, prednisolamate, prednisolone, prednisone, predníval, prednylidene, pregabalin, pregnadiol, pregnenolone, premafloxacin, premazepam, prenalterol, prenisteine, prenoverine, prenoxdiazine, prenylamine, pretamazium, pretiadoil, prezatide, pribecaine, pridefine, prideperone, pridinol, prifelone, prifinium, prifuroline, pilocalne, primaperone, primaquine, primidolol, primidone, primycin, prinomastat, prinomide, prinoxodan, pristinol, pristinamycin, prizidilol, proadifen, probarbital, probenecid, probicromil, probucol, procainamide, procaine, procarbazine, procaterol, prochlorperazine, procinolol, procinonide, proclonol, procromil, procyclidine, procymate, prodeconium, prodilidine, prodipine, prodolic acid, profadol, profexalone, proflavine, proflazepam, progabide, progesterone, proglumetacin, proglumide, proheptazine, proligestone, praline, prolintane, prolonium, promazine, promegestone, promestriene, promethazine, promo late, promoxo lane, prontalol, propacetamol, propafenone, propagermanium, propamidine, propanidid, propanocaine, propantheline, proparacaine, propatyl nitrate, propazolamide, propenidazole, propentofylline, propenzolate, properidine, propetamide, propetamfos, propetandrol, propicillin, propikacin, propinetidine, propiomazine, propiocaine, propiram, propisergide, propiverine, propizepine, propofol, propoxate, propoxur, propoxycaine, propoxyphene, propranolol, propyl docetrizoate, propyl gallate, propylhexedrine, propyliodone, propylthiouracil, propyperone, propyphenazone, propyromazine, proquazone, proquinolate, prorenoate, proroxan, prscillardin, prospidium, prostalene, prosulpride, prosultiamine, proterguride, protheobromine, prothipendyl, prothixene, protiofate, protionamide, protirelin, protizinic acid, protokylol, protoporphyrin, protriptyline, proxole, proxibarbal, proxibutene, proxicromil, proxifezone, proxorphan, proxymetacaine, proxyphylline, prozapine, prucalopride, prulifloxacin, pruvanserin, pseudoephedrine, pumafentrine, pumaprazole, pumitepa, pumosetrag, puromycin, pyrabrom, pyrantel, pyrathiazine, pyrazinamide, pyrazofurin, pyricarbate, pyridarone, pyridinol, pyridofylline, pyridostigmine, pyridoxal, pyridoxamine, pyridoxine, pyrilamine, pyrimethamine, pyrimate, pyrinoline, pyrithione, pyrithyldione, pyritidium, pyritinol, pyrophenindane, pyrovalerone, pyroxamine, pyrrobutamine, pyrrocaine, pyrrolifene, pyrroliphene, pyrrolnitrin, pyrroxane, pyrvinium, pytamine, quadazocine, quadrosilan, quatacaine, quazepam, quazinone, quazodine, quazolast, quetiapine, quifenadine, quiflapon, quillifoline, quilostigmine, quinacainol, quinacillin, quinacrine, quinagolide, quinaldine blue, quinapril, quinaprilat, quinazosin, quibolone, quincarbate, quindecamine, quindonium, quindoxin, quinelorane, quinestradol, quinestrol, quinethazone, quinetolate, quinezamide, quinfamide, quingestanol acetate, quingestrone, quinidine, quinine, quinotolast, quinpirole, quinterenol, quitiofos, quinuclium, quinupramine, quinupristin, quipazine, quisultazine, rabeprazole, raclopride, ractopamine, radafaxine, rafoxanide, ragaglitazar, ralitoline, raloxifene, raltitrexed, raluridine, ramatroban, ramciclane, ramelteon, ramifenazone, ramipril, ramiprilat, ramixotidine, ramnodigin, ramnoplanin, ramorelix, ramosetron, ranelic acid, ranimustine, ranimycin, ranirestat, ranitidine, ranolaine, rapacuronium, rasagiline, rasburicase, rathyronine, ravuconazole, razaxaban, razinodil, razobazam, razoxane, rebimastat, reboxetine, recainam, reclazepam, regadenoson, reglitazar, relcovaptan, relomycin, remacemide, remifentanil, remikiren, remiprostol, remoxipride, renanolone, rentiapril, renzapride, repaglinide, reparixin, repinotan, repirinast, repromicin, reproterol, rescimetol, rescinnamine, resequinil, reserpine, resiquimod, resocortol butyrate, resorantel, resorcinol, retapamulin, retelliptine, retigabine, retinol, revaprazan, revatropate, revenast, reviparin, revizinone, revospirone, ribavirin, riboflavin, riboprine, ribostamuycin, ricasetron, ridazolol, ridogrel, rifabutin, rifalazil, rifametane, rifamexil, rifamide, rifampin, rifapentine, rifaximin, rilapine, rilmakalim, rilmazafone, rilmenidine, rilopirox, rilozarone, rilpovorine, riluzole, rimantadine, rimazolium, rimcazole, rimexolone, rimiterol, rimonabant, rimoprogin, riodipine, rioprostil, ripazepam, ripisartan, risarestat, risedronicacid, risocaine, risotilide, rispenzepine, risperidone, ristianol, ristocetin, ritanserin, ritometan, ritipenem, ritobegron, ritodrine, ritolukast, ritonavir, ritropirronium, ritrosulfan, rivaroxaban, rivastigmine, rivoglitazone, rizatriptan, robalzotan, robenidine, rocastine, rocepafant, rociclovir, rocuronium, rodocaine, rodorubicin, rofecoxib, rofelodine, rofleponide, roflumilast, rogletimide, rokitamycin, rolafagrel, roletamide, rolgamidine, rolicyclidine, rolicyprine, rolipram, rolitetracycline, rolodine, rolziracetam, romazarit, romergoline, romifenone, romifidine, romurtide, ronactolol, ronidazole, ronifibrate, ronipamil, runnel, ropinirole, ropitoin, ropivacaine, ropizine, roquinimex, rosaprostol, rosaramicin, rose bengal, rosiglitazone, rosoxacin, rostafuroxin, rostaporfin, rosterolone, rosuvastatin, rotamicillin, rotigotine, rotoxamine, rotaxate, roxadimate, roxarsone, roxatidine acetate, roxibolone, roxifiban, roxindole, roxithromycin, roxolonium, roxoperone, rubitecan, ruboxistaurin, rufinamide, rufloxacin, rupatadine, rupintrivir, rutamycin, ruvazone, ruzadolane, sabarubicin, sabcomeline, sabeluzole, sabiporide, saccharin, safingol, safirinol, sagandipine, salacetamide, salafibrate, salantel, salazodine, salazosulfadimidine, salazosulfamide, salazosulfathiazole, salcaprozoic acid, salcolex, salethamide, salflucerine, salicyl alcohol, salicylamide, salicylic acid, salinazid, salinomycin, salmefamol, salmeterol, salmisteine, salnacedin, salprotoside, salsalate, sameridine, samixogrel, sampatrilat, sampirtine, sancycline, sanfetrinem, sanguinarium, saperconazole, saprisartan, sapropterin, saquinavir, sarafloxacin, sarakalim, saralasin, sarcolysin, sardomozide, saredutant, saripedem, sarizotan, sarmazenil, samoxicillin, sarpicillin, sarpogrelate, saterinone, satigrel, satranidazole, satraplatin, saviprazole, savoxepin, scopafungin, scopinast, scopolamine, secalciferol, seclazone, secnidazole, secobarbital, securinine, sedecamycin, sedoxantrone, seganserin, segesterone, seglitide, selamectin, selgiline, selfotel, soldenoson, selprazine, sampimod, sematilide, semaxanib, semduramicin, semorphone, semotiadil, semustine, senazodan, seocalcitol, sepazonium, seperidol, sepimostat, seprilose, seproxetine, sequifenadine, seratrodast, serazapine, serfibrate, sergolexole, sermetacin, sertindole, sertraline, setastine, setzindol, setipafant, setiptiline, setoperone, sevitropium, sevopramide, sezalamide, sagoside, sibenadet. Sibopirdine, sibrafiban, sibutramine, siccanin, sifaprazine, siguazodan, silandrone, sildenafil, silibinin, silcristin, sildianin, silodosin, silodrate, silperisone, siltenzepine, simendan, simetride, simfibrate, simtrazene, simvastatin, sincalide, sinefungin, sinitrodil, sintropium, sipatrigine, siramesine, siratiazem, sirolimus, sisomicin, sitafloxacin, sitalidone, sitamaquine, sitaxentan, sitofibrate, sitoglusoide, sivelestat, soblidotin, sobuzoxane, solabegron, solifenasin, solimastat, solpecainol, solypertine, somatadine, soneclosan, sonepiprazole, sopitazine, sopromidine, soquinolol, sorafenib, soraprazan, sorbinicate, sorbinil, sorivudine, sornidipine, sotalol, soterenol, spaglumic acid, sparfloxacin, sparfosate, sparsomycin, sparteine, spectinomycin, spiclamine, spiperone, spiradoline, spiramide, spiramycin, spirapril, spiraprilat, spirendolol, spirgetine, spirilene, spiriprostil, spirofylline, spirogermanium, spiroglumide, spiromustine, spironolactone, spiroplatin, spirorenone, spirotriazine, spiroxasone, spiroxatrine, spiroxepin, spizofurone, sprodiamine, squalamine, squalane, stacofylline, stallimycin, stannsoprfin, stanolone, stanozolol, stavudine, stearylsufamide, steffimycin, stenbolone, stepronin, stercuronium, stevaladil, stibamine, stibophen, stilbamidine, stilbazium, stilonium, strimazole, stiripentol, stirocamide, stirofos, streptomycin, streptonicozid, streptonigrin, streptozocin, styramine, subathiazone, subendazole, succinylcholine, succinylsulfathiazole, succisulfone, suclofenide, sucralfate, sucralose, sucrose octaacetate, sucrosufate, sudexanox, sudoxicam, sufenatil, sufotidine, sufugolix, sugammadex, sulamserod, sulazepam, sulazuril, sulbactam, sulbenicillin, sulbenox, sulbentine, sulbutiamine, sulclamine, sulconazole, sulfabenz, sulfabenzamide, sulfabromomethazine, sulfacarbamide, sulfacecole, sulfacetamide, sulfachlorpyridazine, sulfachrysoidine, sulfaclomide, sulfaclorazole, sulfaclozine, sulfacytine, sulfadiazine, sulfadimethoxine, sulfadoxine, sulfaethidole, sulfaguanidine, sulfaguanole, sulfalene, sulfaloxic acid, sulfamazone, sulfamerazine, sulfameter, sulfamethaziine, sulfamethizole, sulfamethoxazole, sulfamethoxypyridazine, sulfametmidine, sulfametrole, sulfamonomethoxine, sulfamoxole, sulfanilamide, sulfanilate, sulfaanitran, sulfaperin, sulfaphenazole, sulfaproxyline, sulfapyridine, sulfaquinoxaline, sulfarsphenamine, sulfasalazine, sulfasomizole, sulfasuccinamide, sulfasymazine, sulfathiazole, sulfathiourea, sulfatolamide, sulfatroxazole, sulfatrozole, sulfazamet, sulfinaolol, sulfinpyrazone, sulfuram, sulfisomidine, sulfisoxazole, sulfobromophthalein, sulfonterol, sulforidazine, sulfosalicylic acid, sulfoxone, sulcrinat, sulindac, sulisatin, sulisobenzone, sulmarin, sulmazole, sulmepride, sulnidazole, sulocarbilate, suloctidil, sulodexide, sulofenur, sulopenem, sulosemide, sulotroban, suloxifen, sulpiride, sulprosal, sulprostone, sultamicillin, sultiame, sultopride, sultosilic acid, sultroponium, sulukast, sulverapride, sumacetamol, sumanirole, sumarotene, sumatriptan, sumetizide, sunagrel, suncillin, sunepitron, supidimide, supalast, suproclone, suprofen, suramin, suricamide, suriclone, suritozole, suronacrine, susalimod, suxemerid, suxethonium, suxibuzone, symclosene, synetine, tabilautide, tabimorelin, tacalcitol, tacapenem, tacedinaline, taclamine, tacrine, tacrolimus, tadalafil, tafluposide, taglutamine, tagorizine, talampanel, talampicillin, talaporfin, talastine, talbutal, taleranol, talibegron, talinolol, talipexole, talisomycin, tallimustine, talmetacin, talmetoprim, talnetant, talniflumate, talopram, talsalate, toloximine, talsaclidine, talsupram, taltirelin, taltobulin, taltrimide, taludipine, talviraline, tameridone, tameticillin, tametraline, tamibarotene, tamitinol, tanolarizine, tamoxifen, tampramine, tamsulosin, tanaproget, tandamine, tandospirone, tandutinib, taniplon, tanomastat, tapentadol, taprizosin, taprostene, tarazepide, tariquindar, tasosartan, tasuldine, taurolidine, tauromustine, tauroselcholic acid, taurosteine, tazadolene, tazanolast, tazarotene, tazasubrate, tazeprofen, tazifylline, taziprinone, tazobactam, tazofelone, tazolol, tazometine, tebanicline, tebatizole, tebipenem, tebufelone, tebuquine, tecadenoson, tecalcet, tecastemizole, teclthiazide, teclozan, tedisamil, tefazoline, tefenperate, teflufazine, tefiutixol, tegafur, tegaserod, teglicar, teicopanin, telavancin, telbivudine, telenzepine, telinavir, telithromycin, telmesteine, telmisartan, teloxantrone, teludipine, temafioxacin, temarotene, tematropium, temazepam, temefos, temelastine, temiverine, temocapril, temocaprilat, temocillin, temodox, temoporfin, temozolomide, temisirolimus, temurtide, tenamfetamine, tenatoprazole, tendamistat, tenidap, tenilapine, teniloxazine, tenilsetam, teniposide, tenivastatin, tenocyclidine, tenofovir, tenofovir disoproxil, tenonitrozole, tenosal, tenosiprol, tenoxicam, tenylidone, teoprantil, teoprolol, tepirindole, tepoxalin, teprenone, teprotide, terazosin, terbequinil, terbinafine, terbogrel, terbucromil, terbufirol, terbuficin, terbuprol, terbutaline, terciprazine, terconazole, terdecamycin, teerestigmine, terfeadine, terfiavoxate, terfuranol, terguride, teriflunomide, terikalant, terizidone, terlakiren, terlipressin, ternidazole, terodiline, terofenamate, teroxalene, teroxirone, tertatolol, tesaglitazar, tesicam, tesimide, tesimilifene, tesofensine, testolactone, testosterone, tetomilst, tetrabarbital, tetrabenazine, tetracaine, tetracycline, tetrahydrozoline, tetramethrin, tetramisole, tetraxetan, tetrazepam, tetrazolast, tetriprofen, tetrofosmin, tetronasin, tetroquinone, tetroxoprin, tetrydamine, teverelix, texacromil, tezacitabine, tezosentan, thalidomide, thebacon, thenalidine, thenium, thenyldiamine, theobromine, theodrenaline, theofibrate, theophylline, thiabendazole, thiacetarsamide, thialbarbital, thiamazole, thiamine, thiamiprine, thiamphenicol, thamylal, thiazesim, thiazinamium, thiazolsulfone, thiethyperazine, thihexinol ethylbromide, thimerfonate, thimerosal, thiocolchicoside, thioctic acid, thiofuradene, thioguanine, thiohexamide, thioinosine, thiopental, thiophanate, thiopropazate, thioproperazine, thioridazine, thiosalan, thiostrpton, thiotepa, thiotetrabarbital, thiothixene, thiphenamil, thiphencillin, thiram, thonzonium, thonzylamine, thozalinone, threonine, thymocartin, thymoctonan, thymol, thymopentin, thymotrinan, thyromedan, thyropropic acid, thyroxin, tiacrilast, tiadenol, tiafibrate, tiagabine, tiamenidine, tiametomnium, tiamulin, tianafac, tianeptine, tiapamil, tiapirinol, tiapride, tiaprofenic acid, tiaprost, tiaramide, tiazofurin, tiazuril, tiabalosin, tibeglisene, tibenelast, tibenzate, tibezonium, tibolone, tibric acid, tibrofan, ticabesine, ticalopride, ticarbodine, ticarcillin, ticlatone, ticlopidine, ticolubant, ticrynafen, tidembersat, tidiacic acid, tiemonium, tienocarbine, tienopramine, tienoxolol, tifemoxone, tifenazoxide, tiflamizole, tiflorex, tifluadom, tiflucarbine, tiformin, tifurac, tigecycline, tigemonam, tigestol, tigloidine, tilargenine, tiletamine, tilidine, tiliquinol, tilisolol, tilmacoxib, tilmicosin, tilnoprofen, tilomisole, tilorone, tilozepine, tilsuprost, tiludonic acid, timcodar, timefurone, timegadine, timelotem, timepidium, timiperone, timirdine, timobesone acetate, timofibrate, timolol, timonacic, timoprazole, tinabinol, tinazoline, timidazole, tinisulpride, tinofedrine, tinoridine, tiocarlide, tioclomarol, tioconazole, tioctilate, tiodazosin, tiodonium, tiomergine, tiomesterone, tioperidone, tiopinate, tiopronin, tiopropamine, tiospirone, tiotidine, tiotropium, tioxacin, tioxamast, tioxaprofen, tioxidazole, tioxolone, tipentosin, tipepidine, tipetropium, tipifarnib, tipindole, tipranavir, tipredane, tiprenolol, tiprinast, tiprodil, tiprostanide, tiportimod, tiqueside, tiquinamide, tiquizium, tiracizine, tirapazamine, tiratricol, tirilazad, tirofiban, tiropramine, tisartan, tisocalcitate, tisocromide, tisopurine, tisoquone, tivanidazole, tiviciclovir, tivirapine, tixadil, tixanox, tixocortol, tizabrin, tizanidine, tizolemide, tizoprolic acid, tobicillin, toborinone, tobramycin, tocamide, tocamphyl, tocladesine, tocofenoxate, tocofibrate, tocophersolan, todralazine, tofenacin, tofetridine, tofimilast, tofisoline, tofispam, tolafentrine, tolamolol, tolazamide, tolboxane, tolbutamide, tolvapone, tolciclate, toldimfos, tolfamide, tolfenamic acid, tolgabide, tolimidone, tolindate, toliodium, toliprolol, tolmesoxide, tometin, tolnaftate, tolnapersine, tolnidamine, toloconium, tolonidine, tolonium, toloxatone, toloxychlorinol, tolpadol, tolpentamide, tolperisone, tolpiprazole, tolpronine, tolpropamide, tolpyrramide, tolquinzole, tolrestat, tolterodine, toltrazuril, tolufazepam, tolvaptan, tolycaine, tomeglovir, tomelukast, tomoglumide, tomoxiprole, tonabersat, tonazocine, topilutamide, topiramate, topixantrone, topotecan, toprilidine, topterone, toquizine, torbafylline, torcetrapib, torcitabine, toremifene, toripristone, torsemide, tosagestin, tosifen, tosufloxacin, tosulur, trabectedin, traboxopine, tracazolate, tradecamide, tralonide, tramadol, tramazoline, trandolapril, trandolaprilat, tranexamic acid, tranilast, transcamide, trantelinium, tranycypromine, trapencaine, trapidil, travoprost, traxanox, traxoprodil, trazitiline, trazium, trazodone, trazolopride, trebenzomine, trecadrine, trecetilide, trefentanil, trelnarizine, treloxinate, trenbolone, trengestone, trenizine, treosulfan, trepibutone, trepipam, trepirium, treprostinil, treptilamine, terquisin, tresperimus, trestolone, trethinium, trethocanoic acid, tretinoin, tretinoin tocoferil, tretoquinol, triacetin, triafungin, triamcinolone, triamcinolone acetonide, triamcinolone benetonide, triamcinolone furetonide, triampyzine, triamternem triaziquone, triazolam, tribendilol, tribenoside, tribromsalan, tribuzone, tricaprilin, tricetamide, trichlorfon, trichlormethiazide, trichlomethine, triciribine, triclabendazole, triclacetamol, triclazate, triclobisonium, triclocarban, triclodazol, triclofenol, triclofos, triclofyllin, triclonide, triclosan, tricyclamol, tridihexethyl, tridolgosir, trientine, triethylenemelamine, trifenagrel, trifezolac, triflocin, triflubazam, triflumidate, triflomeprazine, trifluperazine, trifluperidol, triflupromazine, trifluidine, triflusal, trifosmin, trigevolol, trihexylpheidyl, triletide, trilostane, trimazosin, trimebutine, trimecain, trimedoxime, trimegestone, trimeperidine, trimeprazine, trimetazidine, trimethadone, trimethamide, trimethaphan, trimethidinium, trimethobenzamide, trimethoprim, trimetozine, trimetrexate, trimexiline, trimipramine, trimoprostil, trimoxamine, trioxifene, trioxsalen, tripalmitin, tripamide, triparanol, tripelennamine, triplatin, triprolidine, triptorelin, tritoqualine, trixolane, trizoxime, trocimine, troclosene, trodusquemine, trofosfamide, troglitazone, troleandomycin, tromanttadine, tropabazate, tropanserin, tropapride, tropatepine, tropenziline, tropicamide, tropigline, tropirine, tropisetron, tropodifene, troquidazole, trospectomycin, trospium, trovafloxacin, trovirdine, troxacitabine, troxerutin, troxipide, troxolamide, troxonium, troxypyrrolium, truxicurium, truxipicurium, tryparsamide, tubocurarine, tubulozole, tucaresol, tuclazepam, tulathromycin, tulobuterol, tulopafant, turosteride, tuvatidine, tybamate, tylosin, tymazolin, tyropanoate, tyrosine, tyrothricin, ubenimex, ubidecarenone, ubisindine, ufenamate, ufiprazole, uldazepam, ulifloxacin, uliprisnil, umespirone, undecylenic acid, unoprostone, upenazime, upidosin, uracil, uracil mustard, urapidil, uredepa, uredofos, urefibrate, ursodiol, urulcholic acid, utibapril, utibaprilat, vadocaine, valaciclovir, valconazole, valdecoxib, valdetamide, valdipromide, valethamate, vlaganiciclovir, valine, valnemulin, vlanoctamide, valofane, valomaciclovir, valperinol, valproate, vlaproicacid, valpromide, valrocemide, valrubicin, valsartan, valorcitabine, valtrate, vamicamide, vancomycin, vandetanib, vaneprim, vanitiolide, vanoxerine, vanyldisulfamide, vapiprost, vapreotide, vardenfanil, varenicline, varespladib, vatalanib, vatanidipine, vebufloxacin, vecuronium, vedaclidine, vedaprofen, velaresol, velnacrine, venlafaxine, venritidine, verodoline, veralipride, verapamil, verazide, verilopam, verlukast, verofylline, versetamide, verteporfin, vesnarinone, vestipitant, vetrabutine, vidarabine, vigabatrin, vilazodone, vildaglipin, viloxazine, vinbarbital, vinblastine, vinburnine, vincamine, vincanol, vincofos, vinconate, vincristine, vindeburnol, vindesine, vinpidine, vinflunine, vinformide, vinfosiltine, vinglycinate, vinleucinol, vinleurosine, vinmegallate, vinorelbine, vinpocetine, vinpoline, vinrosidine, vintiamol, vintoperol, vintriptol, vinylbital, vinzolidine, viomycin, viprostol, viqualine, viquidil, virginiamycin, viridofulvin, viroxime, visnadine, visnafylline, vofopitant, voglibose, volazocine, volpristin, voriconazole, vorozole, voxergolide, xaliproden, xamoterol, xanomeline, xanoxic acid, xanthinol, xantifibrate, xantocillin, xantofyl palmitate, xemilofiban, xenalipin, xenazoic acid, xenbucin, xenipentone, xenothiorate, xengloxal, xenylhexenicacid, xenylropium, xibenolol, xibornol, xidecaflur, xilobam, ximelagatran, ximoprofen, ximidamine, xinomiline, sipamide, xipranolol, xorphanol, xylamidine, xylazine, xylocoumarol, xylometazoline, xyloxemine, yohimbic acid, zabicipril, zabiciprilat, zacopride, zafirlukast, zafuleptine, zalcitabine, zalderide, zaleplon, zalospirone, zalitidine, zaltoprofen, zamifenacin, zanamivir, zanapezil, zankiren, zanoterone, zapizolam, zaprinast, zardaverine, zatebradine, zatosetron, zelandopam, zenarestat, zenazocine, zeniplatin, zepastine, zeranol, zetidoline, zidapamide, zidometacin, zidovudine, zifrostilone, zilantel, zilascorb, zileuton, zilpaterol, zimeldine, zimiidoben, zindotrine, zindoxifene, zinconazole, zinostatin, zinterol, zinviroxime, zipeprol, ziprsidone, zocainone, zofenopril, zofenoprilat, zoficonazole, zolamine, zolasartan, zolazepam, zolendronic acid, zolenzepine, zolertine, zolimidine, zoliprofen, zolmitriptan, zoloperone, Zolpidem, zomebazam, zomepirac, zometapine, zonampanel, zoniclezole, zoniporide, zonisamide, zopiclone, zopolrestat, zorbamycin, zorubicin, zosuquidar, zotepine, zoticasone, zoxazolamine, zucapsaicin, zuclomiphene, zuclopenthixol, zylofuramine, and combinations thereof.

In one embodiment, the active pharmaceutical compound includes any suitable pharmaceutical substance with a half-life of from about 16 hours to about 21 hours. In another embodiment, the active pharmaceutical substance has a half-life of from about 16 hours to about 21 hours, about 17 hours to about 21 hours, from about 18 hours to about 21 hours, from about 19 hours to about 21 hours, from about 20 hours to about 21 hours, from about 16 hours to about 17 hours, from about 16 hours to about 18 hours, from about 16 hours to about 19 hours, from about 16 hours to about 20 hours, from about 17 hours to about 18 hours, from about 17 hours to about 19 hours, from about 17 hours to about 20 hours, from about 17 hours to about 21 hours, from about 18 hours to about 19 hours, from about 18 hours to about 20 hours, from about 18 hours to about 21 hours, from about 19 hours to about 20 hours, from about 19 hours to about 21 hours, or from about 20 hours to about 21 hours.

B. Compositions

Exemplary embodiments of the present invention include controlled absorption pharmaceutical formulations for extended release of pharmaceutically active compounds. In some embodiments, the controlled release dosage form is formulated for oral administration of pharmaceutically active agent that is suitable for administration to patients that have difficulty swallowing solid oral dosage forms. In further embodiments, the controlled absorption pharmaceutical formulation can be used with acceptable 'soft food' for use with patients that have difficulty swallowing a tablet, capsule or pill. In some embodiments, the controlled absorption pharmaceutical formulation can be modified for administration of the pharmaceutically active compounds in a gastronasal feeding tube or any other "feeding tube" type apparatus where timed release of the pharmaceutically active compound is desired.

In some embodiments, oral delivery of the controlled absorption pharmaceutical formulation is preferred. Since the pharmaceutical compositions disclosed herein may be delivered by oral administration to patient, including an animal and a human, these compositions may be formulated with an inert diluent or with an assimilable edible carrier, or they may be enclosed in hard- or soft-shell gelatin capsule, or they may be compressed into tablets, or they may be incorporated directly with the food of the diet.

In some embodiments, the pharmaceutical composition of the present invention may be formulated for parenteral delivery. Alternatively, the pharmaceutical composition may be formulated for nasal, buccal, passive transdermal, iontophoretic transdermal, electrophoretic transdermal, microneedle transdermal, or skin ablation transdermal delivery.

In one exemplary embodiment, the controlled release pharmaceutical formulation comprises a particulate composition, said particulate composition comprising (a) a core, said core comprising a pharmaceutically active substance and a set of one or more drug-binding polymers, wherein said pharmaceutically active substance is in reversible association with said set of one or more drug binding polymers; and (b) a membrane, said membrane surrounding said core and comprising a pharmaceutically acceptable film-forming, water insoluble polymer. In one embodiment, the drug-binding polymer comprises methyl cellulose. In another embodiment, the pharmaceutically active substance and the set of one or more drug-binding polymers are present in respective weight ratio of from about 20:1 to about 1:2. In another embodiment, the pharmaceutically active substance and the set of one or more drug-binding polymers are present in respective weight ratio of about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, about 5:1, about 4:1, about 3:1, about 2:1, about 19:2, about 17:2, about 15:2, about 13:2, about 11:2, about 9:2, about 7:2, about 5:2, about 4:2, about 3:2, or about 2:1.

In one exemplary embodiment, the controlled absorption composition comprises naproxen as the pharmaceutically active substance. In another exemplary embodiment, the controlled absorption composition comprises a naproxen salt as the pharmaceutically active substance. In a specific embodiment, the controlled absorption composition comprises free acid as the pharmaceutically active substance. In another specific embodiment, the controlled absorption composition comprises naproxen sodium salt as the pharmaceutically active substance.

The particles of the compositions for use in accordance with the invention may be of any desired shape. Exemplary shapes include spheroidal, plates, shards, fibers, cuboidal, sheets, rods, oval, strings, elongated particles, wedges, discs, rectangular, polyhedral, etc. In accordance with the invention it is of advantage if they have a spheroid shape. In the context of the present invention, a spheroid shape is a shape substantially like that of a ball. Examples of spheroidal shapes include beads, egg-shaped particles, dodecahedra or icosahedra, which may also have certain irregularities.

In some embodiments, the particles have a median or mean diameter of from about 0.1 mm to about 0.9 mm. In other embodiments, the average diameter of particles in the particulate composition is 0.8 mm. In general, the median or mean diameter of particles in the composition in accordance with the present invention ranges from 0.2 mm to 0.9 mm, from 0.3 mm to 0.9 mm, from 0.4 mm to 0.9 mm, from 0.5 mm to 0.9 mm, from 0.6 mm to 0.9 mm, from 0.7 mm to 0.9 mm, from 0.8 mm to 0.9 mm, from 0.1 mm to 0.2 mm, from 0.1 mm to 0.3 mm, from 0.1 mm to 0.4 mm, from 0.1 mm to 0.5 mm, from 0.1 mm to 0.6 mm, from 0.1 mm to 0.7 mm, from 0.1 mm to 0.8 mm, from 0.2 mm to 0.3 mm, from 0.2 mm to 0.4 mm, from 0.2 mm to 0.5 mm, from 0.2 mm to 0.6 mm, from 0.2 mm to 0.7 mm, from 0.2 mm to 0.8 mm, from 0.3 mm to 0.4 mm, from 0.3 mm to 0.5 mm, from 0.3 mm to 0.6 mm, from 0.3 mm to 0.7 mm, from 0.3 mm to 0.8 mm, from 0.4 mm to 0.5 mm, from 0.4 mm to 0.6 mm, from 0.4 mm to 0.7 mm, from 0.4 mm to 0.8 mm, from 0.5 mm to 0.6 mm, from 0.5 mm to 0.7 mm, from 0.5 mm to 0.8 mm, from 0.6 mm to 0.7 mm, or from 0.7 mm to 0.8 mm.

Thus, particle properties can be valuable indicators of quality and performance of particulate materials in pharmaceutical applications. In the case of particle size, several particle size measuring methods exists, including volume-, weight- and area-based particle size measuring techniques. These particle size measuring methods include light-based methods, ultrasound, electric field, gravity, and centrifugation-based methods. Laser diffraction results, for example, are reported on a volume basis and so volume mean can be used to define the central point although the median is more frequently used than the mean when using this technique. Particles size distributions disclosed herein were determined by microphotography, area-based particle size measuring technique. Integrating size of the particles, area was obtained from which the diameters of the particles were calculated.

FIGS. 6 and 7 respectively illustrate particle distributions for exemplary Formulations 2 and 4. As illustrated in these figures a particulate composition according to the present invention can comprises microparticles/microparticulates having a range of particle sizes. A percentage of particles having a given range of particle diameter can be calculated based on these figures according to the following formula:

$$\text{percentage of particles} = \frac{n(i) \times 100\%}{n(t)},$$

wherein n(i) is the number of particles having a specific range of particle diameter and n(t) is the total particle count in the sample. In FIG. 6, for example, n(t)=(6+15+16+10+3+2+1+5+1)=59, the percentage of particles having particle diameter range of 102-207 mm is (6/59)×100%≈10.2%. This calculation can be performed for each of range of particle diameter. A similar set of calculations can be carried out for the particle distribution in FIG. 7 to determine the percentage of particles within each range of particle diameters.

Accordingly, in some embodiments of the particulate composition of the present invention: about 10% of the particles have a particle diameter of at least about 102 μm but equal or less than about 207; about 35% of the particles have a particle diameter of at least about 102 μm but equal or less than about 313; about 62% of the particles have a particle diameter of at least about 102 μm but equal or less than about 419; about 79% of the particles have a particle diameter of at least about 102 μm but equal or less than about 525; about 84% of the particles have a particle diameter of at least about 102 μm but equal or less than about 631; about 88% of the particles have a particle diameter of at least about 102 μm but equal or less than about 737; about 89% of the particles have a particle diameter of at least about 102 μm but equal or less than about 949; about 98% of the particles have a particle diameter of at least about 102 μm but equal or less than about 1055; at least about 99% of the particles have a particle diameter of at least about 102 μm but equal or less than about 1267.

In some embodiments of the particulate composition of the present invention: about 7% of the particles have a particle diameter of at least about 179 μm but equal or less than about 240 μm; about 14% of the particles have a particle diameter of at least about 179 μm but equal or less than about 302 μm; about 37% of the particles have a particle diameter of at least about 179 μm but equal or less than about 364 μm; about 53% of the particles have a particle diameter of at least about 179 μm but equal or less than about 426 μm; about 74% of the particles have a particle diameter of at least about 179 μm but equal or less than about 488 μm; about 87% of the particles have a particle diameter of at least about 179 μm but equal or less than about 550 μm; about 90% of the particles have a particle diameter of at least about 179 μm but equal or less than about 612 μm; about 93% of the particles have a particle diameter of at least about 179 μm but equal or less than about 674 μm; about 97% of the particles have a particle diameter of at least about 179 μm but equal or less than about 736 μm; and at least about 98% of the particles have a particle diameter of at least about 179 μm but equal or less than about 860 μm.

In some embodiments, a particulate composition in accordance with the present invention comprises a particle distribution wherein about 99% of the particles have a particle diameter of about 1267 μm or less. In some embodiments, said particle size distribution is selected from the group consisting of: about 98% of particles having a particle diameter of about 1055 μm or less; about 89% of particles having a particle diameter of about 949 μm or less; about 87% of particles having a particle diameter of about 737 μm or less; about 84% of particles having a particle diameter of about 631 μm or less; about 79% of particles having a particle diameter of about 525 μm or less; about 62% of particles having a particle diameter of about 419 μm or less; about 35% of particles having a particle diameter of about 313 μm or less; and about 10% of particles having a particle diameter of about 207 μm or less.

In some embodiments, a particulate composition in accordance with the present invention comprises a particle distribution wherein about In one embodiment, a particulate composition according to the present invention comprises microparticles/microparticulates having average diameter of from about 100 μm to about 900 μm. In another embodiment, said particulate composition comprises microparticles/microparticulates having average diameter selected from the group consisting of: from 100 μm to about 150 μm; from about 150 μm to about 200 μm; from about 200 μm to about 250 μm; from about 250 μm to about 300 μm; from about 300 μm to about 350 μm; from about 350 μm to about 400 μm; from about 400 μm to about 450 μm; from about 450 μm to about 500 μm; from about 500 μm to about 550 μm; from about 550 μm to about 600 μm; from about 600 μm to about 650 μm; from about 650 μm to about 700 μm; from about 700 μm to about 750 μm; from about 750 μm to about 800 μm; from about 800 μm to about 850 μm; from about 850 μm to about 900 μm; from about 150 μm to about 200 μm; from about 200 μm to about 250 μm; from about 250 μm to about 300 μm; from about 300 μm to about 350 μm; from about 350 μm to about 400 μm; from about 400 μm to about 450 μm; from about 450 μm to about 500 μm; from about 500 μm to about 550 μm; from about 550 μm to about 600 μm; from about 600 μm to about 650 μm; from about 650 μm to about 700 μm; from about 700 μm to about 750 μm; from about 750 μm to about 800 μm; from about 800 μm to about 850 μm; from about 200 μm to about 250 μm; from about 250 μm to about 300 μm; from about 300 μm to about 350 μm; from about 350 μm to about 400 μm; from about 400 μm to about 450 μm; from about 450 μm to about 500 μm; from about 500 μm to about 550 μm; from about 550 μm to about 600 μm; from about 600 μm to about 650 μm; from about 650 μm to about 700 μm; from about 700 μm to about 750 μm; from about 750 μm to about 800 μm; from about 250 μm to about 300 μm; from about 300 μm to about 350 μm; from about 350 μm to about 400 μm; from about 400 μm to about 450 μm; from about 450 μm to about 500 μm; from about 500 μm to about 550 μm; from about 550 μm to about 600 μm; from about 600 μm to about 650 μm; from about 650 μm to about 700 μm; from about 700 μm to about 750 μm; from about 300 μm to about 350 μm; from to about 350 μm to about 400 μm; from to about 400 µm to about 450 µm; from to about 450 µm to about 500 µm; from about 350 µm to about 400 µm; from to about 400 µm to about 450 µm; from about 450 µm to about 500 µm and combinations thereof.

In another embodiment, a particulate composition according to the present invention has a particle size distribution wherein at least 98% of the particles have a diameter of about 860 µm or less. In another embodiment, said particle size distribution is selected from the group consisting of: about 97% of particles having a particle diameter of about 798 µm or less; about 93% of particles having a particle diameter of about 736 µm or less; about 92% of particles having a particle diameter of about 674 µm or less; about 90% of particles having a particle diameter of about 612 µm or less; about 87% of particles having a particle diameter of about 550 µm or less; about 74% of particles having a particle diameter of about 488 µm or less; about 53% of particles having a particle diameter of about 426 µm or less; about 37% of particles having a particle diameter of about 364 µm or less; about 14% of particles having a particle diameter of about 302 µm or less; about and 7% of particles having a particle diameter of about 240 µm or less.

In another embodiment, a particulate composition according to the present invention has a particle size distribution wherein the smallest particle has a diameter of at least 102 µm As for irregularly shaped particles, the recited dimension ranges may represent the length of the greatest or smallest dimension of the particle. As examples, the particles can be pin shaped, with tapered ends having an average diameter of from about 0.2 mm to about 0.8 mm. As will be appreciated by one of skill in the art, the maximum particle size will depend in part on whether the composition will effect satisfactory controlled release of the active pharmaceutical substance.

In some exemplary embodiments, the controlled absorption composition comprises a sufficient quantity of a rapid release form of the pharmaceutically active substance to ensure prompt achievement of desired plasma levels of the pharmaceutically active substance together with a sustained release form of the pharmaceutically active substance for prolonged biological effects. In one embodiment, the controlled absorption composition comprises rapid and prolonged release components that preferably have a dissolution rate which when measured in a type 1 dissolution basket apparatus according to U.S. Pharmacopoeia XXII in phosphate buffer at pH 7.2 and at 75 r.p.m. substantially corresponds to the following dissolution pattern: (a) from 15 to 50% of the total pharmaceutically active substance is released after 0.5 hours of measurement in said apparatus; (b) from 25 to 75% of the total pharmaceutically active substance is released after 1 hour of measurement in said apparatus; (c) not less than 65% of the total pharmaceutically active substance is released after 4 hours of measurement in said apparatus. In one embodiment, the pharmaceutically active substance is naproxen sodium salt. In another embodiment, the pharmaceutically active substance is naproxen free acid. In one embodiment, the controlled absorption composition adapted to oral administration of naproxen, and including a sufficient quantity of a rapid release form of naproxen to ensure prompt achievement of analgesically effective blood levels together with the prolonged effects described above.

In one embodiment, the twice a day administration is reduced to once a day administration by extending the release profiling by 2 hours or 2-4 hours, or 3-8 hours while still maintaining efficacious blood levels of the pharmaceutically active substance.

In another embodiment, the controlled absorption composition comprises rapid and prolonged release components such that when its dissolution rate is measured in vitro in a type 2 dissolution paddle apparatus according to U.S. Pharmacopoeia XXII in phosphate buffer at pH 7.4 and at 50 r.p.m. the dissolution rate substantially corresponds to the following dissolution pattern: (a) from 25% to 60% of the total pharmaceutically active substance is released after 0.5 hours of measurement in said apparatus; (b) from 35% to 75% of the total pharmaceutically active substance is released after 1 hour of measurement in said apparatus; and (c) not less than 65% of the total pharmaceutically active substance is released after 4 hours of measurement in said apparatus. In one embodiment, the pharmaceutically active substance is naproxen sodium salt. In another embodiment, the pharmaceutically active substance is naproxen free acid. In one embodiment, the controlled absorption composition adapted to oral administration of naproxen, and including a sufficient quantity of a rapid release form of naproxen to ensure prompt achievement of analgesically effective blood levels together with the prolonged effects described above.

While exemplary embodiments described herein use naproxen sodium to illustrate aspects of the present invention, it will be understood by those skilled in the art that any suitable pharmaceutically active compound can be used. Examples of pharmaceutically active compounds that may be used with the composition of the present invention are given in Section A above.

In one embodiment, a naproxen formulation for oral administration comprises particulates as described herein, said formulation including a sufficient quantity of a rapid release form of naproxen to ensure prompt achievement of analgesically effective blood levels together with a sustained release form of naproxen for prolonged analgesic effects. In an embodiment, the formulation comprises rapid and prolonged release components, preferably having a dissolution rate which when measured in a type 1 dissolution basket apparatus according to U.S. Pharmacopoeia XXII in phosphate buffer at pH 7.2 and at 75 r.p.m. substantially corresponds to the following dissolution pattern: (a) from 15 to 50% of the total naproxen is released after 0.5 hours of measurement in said apparatus; (b) from 25 to 75% of the total naproxen is released after 1 hour of measurement in said apparatus; (c) not less than 65% of the total naproxen is released after 4 hours of measurement in said apparatus.

In another embodiment, the formulation of naproxen comprises rapid and prolonged release components. Preferably, when dissolution rate of the naproxen formulation is measured in vitro in a type 2 dissolution paddle apparatus according to U.S. Pharmacopoeia XXII in phosphate buffer at pH 7.4 and at 50 r.p.m. the dissolution rate substantially corresponds to the following dissolution pattern: (a) from 25 to 60% of the total naproxen is released after 0.5 hours of measurement in said apparatus; (b) from 35 to 75% of the total naproxen is released after 1 hour of measurement in said apparatus; and (c) not less than 65% of the total naproxen is released after 4 hours of measurement in said apparatus.

In another preferred embodiment, the set one or more drug-binding polymers are selected from the group comprising: methyl cellulose, ethyl cellulose, carboxy methylcellulose, diethylaminoethyl cellulose and other suitable matrixes which have the ability to bind the pharmaceutical agent through ionic attraction, or weak hydrogen bonding.

In a further embodiment, the core of the particulate composition of the present invention can contain a lubricant. In one embodiment, the lubricant comprises sodium stearate, magnesium stearate, stearic acid, talc or combinations thereof. Generally, the pharmaceutically active agent and the lubricant are preferably present in a weight ratio of from about 10:1 to about 200:1. In another embodiment, the pharmaceutically active agent and the lubricant are preferably present in a weight ratio of about 11:1, about 12:1, about 13:1, about 14:1, about 15:1, about 16:1, about 17:1, about 18:1, about 19:1, about 20:1, about 21:1, about 22:1, about 23:1, about 24:1, about 25:1, about 26:1, about 27:1, about 28:1, about 29:1, about 30:1, about 31:1, about 32:1, about 33:1, about 34:1, about 35:1, about 36:1, about 37:1, about 38:1, about 39:1, about 40:1, about 41:1, about 42:1, about 43:1, about 44:1, about 45:1, about 46:1, about 47:1, about 48:1, about 49:1, about 50:1, about 51:1, about 52:1, about 53:1, about 54:1, about 55:1, about 56:1, about 57:1, about 58:1, about 59:1, about 60:1, about 61:1, about 62:1, about 63:1, about 64:1, about 65:1, about 66:1, about 67:1, about 68:1, about 69:1, about 70:1, about 71:1, about 72:1, about 73:1, about 74:1, about 75:1, about 76:1, about 77:1, about 78:1, about 79:1, about 80:1, about 81:1, about 82:1, about 83:1, about 84:1, about 85:1, about 86:1, about 87:1, about 88:1, about 89:1, about 90:1, about 91:1, about 92:1, about 93:1, about 94:1, about 95:1, about 96:1, about 97:1, about 98:1, about 99:1, about 100:1, about 101:1, about 102:1, about 103:1, about 104:1, about 105:1, about 106:1, about 107:1, about 108:1, about 109:1, about 110:1, about 111:1, about 112:1, about 113:1, about 114:1, about 115:1, about 116:1, about 117:1, about 118:1, about 119:1, about 120:1, about 121:1, about 122:1, about 123:1, about 124:1, about 125:1, about 126:1, about 127:1, about 128:1, about 129:1, about 130:1, about 131:1, about 132:1, about 133:1, about 134:1, about 135:1, about 136:1, about 137:1, about 138:1, about 139:1, about 140:1, about 141:1, about 142:1, about 143:1, about 144:1, about 145:1, about 146:1, about 147:1, about 148:1, about 149:1, about 150:1, about 151:1, about 152:1, about 153:1, about 154:1, about 155:1, about 156:1, about 157:1, about 158:1, about 159:1, about 160:1, about 161:1, about 162:1, about 163:1, about 164:1, about 165:1, about 166:1, about 167:1, about 168:1, about 169:1, about 170:1, about 171:1, about 172:1, about 173:1, about 174:1, about 175:1, about 176:1, about 177:1, about 178:1, about 179:1, about 180:1, about 181:1, about 182:1, about 183:1, about 184:1, about 185:1, about 186:1, about 187:1, about 188:1, about 189:1, about 190:1, about 191:1, about 192:1, about 193:1, about 194:1, about 195:1, about 196:1, about 197:1, about 198:1, about 199:1, or about 200:1.

The membrane forming polymeric material suitable for use in the present invention may be rapidly soluble in water or insoluble in water or freely permeable to naproxen and water.

As used herein, the term water soluble polymer includes polymers which are freely permeable to water.

As used herein, the term water insoluble polymer includes polymers which are slightly permeable to water.

In some embodiments, the membrane forming polymeric material preferably consists solely of a water insoluble polymer or a polymer which is slightly permeable to water and aqueous solutions of the pharmaceutically active substance, including aqueous solutions of naproxen. In alternative embodiments, the membrane forming polymeric material may consist solely of a water soluble polymer or a polymer which is freely permeable to aqueous solutions of naproxen and water.

In some embodiments, the polymeric material of the core may include a combination of a water insoluble polymer with a water soluble polymer. In some embodiments, the ratio of water soluble/freely permeable to water insoluble/slightly permeable polymer is determined by the particular combination of polymers selected.

In one embodiment, the water soluble polymer is selected from the group consisting polyvinyl alcohol, polyvinylpyrrolidone, methyl cellulose, hydroxypropyl cellulose, ethyl cellulose, agar, carrageenan, xanthan, hydroxypropylmethyl cellulose or polyethylene glycol and combinations thereof. In a preferred embodiment, the water soluble polymer is ethylcellulose.

In some embodiments, the water insoluble polymer of the core is selected from the group consisting of ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly (ethylene), poly (ethylene) low density, poly(ethylene) high density, poly (propylene), poly(ethylene oxide), poly(ethylene terephthalate), poly(vinyl isobutyl ether), poly(vinyl acetate), poly(vinyl chloride) or polyurethane and combinations thereof.

In an embodiment, the water insoluble polymer of the core may comprise naturally occurring polymers and/or resins. In a preferred embodiment, the water insoluble, naturally occurring polymers include shellac, chitosan, gum juniper and combinations thereof.

In one embodiment, a suitable polymer which is slightly permeable to exemplary pharmaceutically active substances, including naproxen, and water is a polymer sold under the Trade Mark EUDRAGIT RS or a polymer whose permeability is pH dependent and sold under the Trade Mark EUDRAGIT L, EUDRAGIT S or EUDRAGIT E. In a preferred embodiment, the slightly permeable polymers include of the categories EUDRAGIT RS and EUDRAGIT L and a combination thereof.

EUDRAGIT polymers are polymeric lacquer substances based on acrylates and/or methacrylates. The polymeric materials sold under the Trade Marks EUDRAGIT RL and EUDRAGIT RS are acrylic resins comprising copolymers of acrylic and methacrylic acid esters with a low content of quaternary ammonium groups and are described in the "EUDRAGIT" brochure of Messrs. Rohn Pharma GmbH (1985) wherein detailed physical-chemical data of these products is given. The ammonium groups are present as salts and give rise to the permeability of the lacquer films. EUDRAGIT RL and RS are freely permeable (RL) or slightly permeable (RS), respectively, independent of pH.

EUDRAGIT L is an anionic polymer synthesized from methacrylic acid and methacrylic acid methyl ester. It is insoluble in acids and pure water. It becomes soluble in a neutral to weakly alkaline milieu by forming salts with alkalis. The permeability of EUDRAGIT L is pH dependent. Above pH 5.0, the polymer becomes increasingly permeable. EUDRAGIT L is described in the "EUDRAGIT L" brochure of Messrs. Rohn Pharma GmbH (1986) wherein detailed physical-chemical data of the product is given.

In an exemplary composition, naproxen and binding polymer are blended to form a homogenous powder. In some preferred embodiments, the naproxen component and binding polymer component are present in a weight ratio of from about 20:1 to about 1:2. In some preferred embodiments, the naproxen component and binding polymer component are present in a weight ratio of from about 6:1 to 1:1. In one embodiment, the blend may be passed through an appropriate mesh screen using a milling machine.

In a further embodiment, the core may optionally contain a lubricant. In one embodiment, the pharmaceutically active substance, including naproxen, and the lubricant are in a weight ratio ranging from about 50:1 to about 5:1. In another embodiment, the weight ratio of the pharmaceutically active substance, including naproxen, to the lubricant is about 50:1, about 49:1, about 48:1, about 47:1, about 46:1, about 45:1, about 44:1, about 43:1, about 42:1, about 41:1, about 40:1, about 39:1, about 38:1, about 37:1, about 36:1, about 35:1, about 34:1, about 33:1, about 32:1, about 31:1, about 30:1, about 29:1, about 28:1, about 27:1, about 26:1, about 25:1, about 24:1, about 23:1, about 22:1, about 21:1, about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, or about 5:1.

In some preferred embodiments, the coating materials include solutions/suspensions of the polymers cited for use in the application of the powder blend to the central cores in a suitable organic/aqueous carrier medium.

In one embodiment, the membrane of the film-forming polymer or mixture of polymers surrounding the core preferably has a proportion of a polymer which is slightly permeable to the pharmaceutically active substance, including naproxen, and water and optionally a proportion of a water permeable polymer, the ratio of slightly water permeable to water permeable polymer being determined by the inherent permeability characteristics of the polymer selected.

In some embodiments, the membrane of the film-forming polymer or mixture of polymers surrounding the core preferably may comprise a proportion of a polymer which is water insoluble and a proportion of a polymer which is water soluble, the ratio of the water insoluble polymer to the water soluble polymer being determined by the inherent permeability of the respective polymers.

In general, the ratio of water insoluble/slightly permeable polymers to water soluble/permeable polymers ranges from about 1:5 to about 50:1. In some embodiments, the ration ranges from about 1:2 to about 20:1. In one embodiment, the ratio is about 50:1, about 49:1, about 48:1, about 47:1, about 46:1, about 45:1, about 44:1, about 43:1, about 42:1, about 41:1, about 40:1, about 39:1, about 38:1, about 37:1, about 36:1, about 35:1, about 34:1, about 33:1, about 32:1, about 31:1, about 30:1, about 29:1, about 28:1, about 27:1, about 26:1, about 25:1, about 24:1, about 23:1, about 22:1, about 21:1, about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, or about 5:1. In another embodiment, the ratio is about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, about 5:1, about 4:1, about 3:1, or about 2:1. In yet another embodiment, the ratio is about [0001] about 19:2, about 17:2, about 15:2, about 13:2, about 11:2, about 9:2, about 7:2, about 5:2, or about 3:2. Examples of each of these types of polymer are described above.

The water insoluble polymer of the membrane may also comprise naturally occurring polymers or resins. Suitable water insoluble, naturally occurring polymers include shellac, chitosan, gum juniper and combinations thereof.

The membrane of the film-forming polymer or mixture of polymers surrounding the core may be built up by applying a plurality of coats of membrane polymer solution or suspension to the core. In some embodiments, the membrane solution or suspension contains the polymer(s) dissolved or suspended, respectively, in a suitable aqueous or organic solvent or mixture of solvents. In one embodiment, said organic solvents are selected from the group consisting of ethanol, ethylene bromide, butanol, acetone, chloroform, 2-ethylhexanol, methyl ethyl ketone, ethylene chloride, isobutanol, glycerol, methyl isobutyl ketone, dichloromethane, isopropanol, methyl isopropyl ketone, tetrachloroethylene, methanol, mesityl oxide, carbon tetrachloride, propanol, trichloroethylene, propylene glycol, 1,4-dioxane, butyl ether, dimethylformamide, ethyl ether, diisopropyl ether, dimethyl sulfoxide, tetrahydrofuran, tert-butyl methyl ether, pyridyne, acetonitrile, ethyl acetate, cyclohexane, toluene, hexane, xylene, other suitable solvents, and combinations thereof. In another embodiment, said aqueous solvents include water, water buffered to a specific pH with phosphate or carbonate ions, and combinations of aqueous and one or more organic solvents.

The particulate cores in accordance with the present invention are formulated with sustained release characteristics allowing a continuous supply of the pharmaceutically active substance, including naproxen, to be maintained in the plasma to achieve a prolonged biological effect, including a prolonged analgesic effect in the case of naproxen. On administration of the pharmaceutical formulations in accordance with the present invention, including naproxen formulations, the formulation, preferably a particulate, is combined with a soft food, ingested, whereby ingested composition dissociates over time, releasing the pharmaceutically active substance, e.g. naproxen, over a wide area of the GI tract. In this way, the number of gastrointestinal absorption sites is increased, minimizing the occurrence of adverse GI effects often associated with the administration the pharmaceutically active substances, including NSAID's, and in particulars naproxen. The compositions in accordance with the present invention, including naproxen particulate formulation, therefore are ideally suited to a once-daily dosage regimen having the potential for fewer associated adverse GI effects.

III. Examples

The Examples that follow are illustrative of comparators and embodiments of the invention, and various uses thereof. They are set forth for explanatory purposes only, and are not to be taken as limiting the invention.

The internal core composed of Naproxen (or a suitable salt) and the polymeric matrix may be formed by the following procedures. Following creation of the internal core, the cores were coated with various polymers with limited water and pharmaceutically active organic molecule solubility. The formation of the "sprinkle formulation" is detailed for 5 separate formulations below:

Formulation 1:

Methocel (20 g) and Naproxen sodium (44 g) were blended for 10 minutes in Kitchenaid mixer (Model KSM103) set at 25 RPMs at ambient temperature.

The resultant blend was transferred to fluid bed granulator (Fluid Air Fluid Bed 2 L granulator) set for top spray granulation. The granulation solution (Surelease K-L-7 19040 clear) was diluted to contain 20% solids. The bed was fluidized for 5 minutes prior to beginning the spraying. The Surelease was sprayed at a rate of 5 g per minute with the bed temperature maintained at 30-35 C while coating was being applied. Granulation continued until all granulation was consumed. The granulation was then left in granulator for 2 hrs at 40° C. with the bed fluidized to allow curing of the Surelease.

Formulation 2:

Methocel (56 g) and Naproxen sodium (44 g) were blended for 10 minutes in a Kitchenaid mixer (Model KLM109) set at 25 RPMs at ambient temperature.

The resultant blend was transferred to fluid bed granulator (Fluid Air Fluid Bed 2 L granulator) set for top spray granulation. The granulation solution (Surelease K-L-7 19040 clear) was diluted to contain 20% solids. The bed was fluidized for 5 minutes prior to beginning the spraying. The Surelease was sprayed at a rate of 5 g per minute with the bed temperature maintained at 30-35 C while coating was being applied. Granulation continued until all granulation was consumed. The granulation was then left in granulator for 2 hrs at 40° C. with the bed fluidized to allow curing of the Surelease.

Formulation 3:

Avocel (17 g) and Naproxen sodium (53 g) were blended for 10 minutes in a Kitchenaid mixer (Model KLM103) set at 25 RPMs at ambient temperature.

The resultant blend was transferred to fluid bed granulator (Fluid Air Fluid Bed 2 L granulator) set for top spray granulation. The granulation solution (Eudragit RL 30 D) was diluted to contain 20% solids. The bed was fluidized for 5 minutes prior to solution spray begins. Solution was sprayed at a rate of 15 g per minute with the bed temperature maintained at 30-35° C. while coating was being applied. Granulation continued until all granulation was consumed. The granulation was then left in granulator for 2 hrs at 40° C. with the bed fluidized to allow curing of the Eudragit RL 30 D.

Formulation 4:

Prosolv HD90 (25 g), a silicified high-density microcrystalline cellulose composed of 98% microcrystalline cellulose and 2% colloidal silicon dioxide, and Naproxen sodium (58.3 g) are blended for 10 minutes in a Kitchenaid mixer (Model KLM103) set at 25 RPMs at ambient temperature.

The resultant blend was transferred to fluid bed granulator (Fluid Air Fluid Bed 2 L granulator) set for top spray granulation. The granulation solution (Eudragit NE 30 D) was diluted to contain 20% solids. The bed was fluidized for 5 minutes prior to solution spray begins. Solution was sprayed at a rate of 15 g per minute with the bed temperature maintained at 20-25° C. while coating was being applied. Granulation continued until all granulation was consumed. The granulation was then left in granulator for 2 hrs at 40° C. with the bed fluidized to allow curing of the Eudragit NE30D.

Formulation 5:

Prosolv HD90 (20 g), a silicified high-density microcrystalline cellulose composed of 98% microcrystalline cellulose and 2% colloidal silicon dioxide, and Naproxen sodium (58 g) are blended for 10 minutes in a Kitchenaid mixer (Model KLM103) set at 25 RPMs at ambient temperature.

The resultant blend was transferred to fluid bed granulator (Fluid Air Fluid Bed 2 L granulator) set for top spray granulation. The granulation solution (Eudragit NE 30 D) was diluted to contain 20% solids. The bed was fluidized for 5 minutes prior to solution spray begins. Solution was sprayed at a rate of 15 g per minute with the bed temperature maintained at 20-25° C. while coating was being applied. Granulation continued until all granulation was consumed. The granulation was then left in granulator for 2 hrs at 40° C. with the bed fluidized to allow curing of the Eudragit NE30D.

The finished particulates were dried to evaporate all solvents prior to performing the dissolution test. Following curing, the resultant sprinkle formulations were assayed to determine the naproxen release rate from the "sprinkles." Dissolution testing was performed on the granulations using Elan's Naprelan 375 mg tablet procedure no. 5000000. The testing proceeded as measured in a type 1 dissolution basket apparatus according to U.S. Pharmacopoeia XXII in phosphate buffer at pH 7.2 and at 75 r.p.m. In order to keep the granulation in the test baskets during the dissolution test granulation samples with a particle size between 425 and 600 µm in diameter.

IV. Figures

The accompanying figures are graphs of the percent naproxen released when tested by the method of the U.S. Pharmacopoeia XXII Basket method in phosphate buffer at pH 7.2 and at 75 r.p.m. versus time (hours) for a naproxen formulation according to the present invention relative to two reference naproxen formulations. The naproxen sodium was quantitatively determined using u.v. spectrophotometry at 331 nm.

These data indicate that micro granules incorporating naproxen into the core, when coated with a suitable membrane forming polymer has a release profile which would provide suitable blood concentrations sufficient to produce the desired analgesic and anti-inflammatory effect which would be comparable to a time release tablet for once or twice a day administration. This profile is achieved by the combination of the membrane forming polymer coating the internal pharmaceutically active chemical bound to a polymer.

FIGS. 1 and 2 demonstrate the drug-binding properties of Methocel with respect to preventing the immediate release of naproxen from the particles. FIGS. 3-4 demonstrate that Avocel and Prosolv HD90, a silicified high-density microcrystalline cellulose composed of 98% microcrystalline cellulose and 2% colloidal silicon dioxide, both have appropriate/suitable drug-binding properties matched to release an appropriate/suitable amount of naproxen sufficient to provide for a sustained release.

The Surelease coating was also found to have an unpleasant texture in the mouth when formulated as a 425 and 600 µm in diameter particle.

Although Formulation 3 provided an extended release dissolution profile, Formulation 3 did not release enough naproxen to provide for analgesia and anti-inflammatory response in hours 1-3.

Formulations 4 and 5 provided early release and continued release of naproxen for the 4 hours of the test period. In addition, the formulation was of the correct size, for example, having particle size distribution of from about 105 µm to about 900 µm, and texture to provide for a satisfactory formulation.

In order to provide evidence that particle size by itself/alone did not influence naproxen release, the diameter of particles of a formulation which did provide controlled release over 4 hours (Formulation 4) was compared to the diameter of particles of a formulation which provided instant release over 4 hours (Formulation 2). Particles size was determined by microphotography. The measured size (area) of the particles was integrated to obtain area from which the diameters of the particles were calculated. Selection of particles for analysis was randomized.

When particles for each of the formulations were examined, a sample of the particles from Formulation 4 had fewer "fines" or particles less than 179 µm in diameter while the particles from Formulation 2 exhibited a greater number of "fines" or particles less than 100 µm in diameter. Table 1 below describes the average particle size and number of fines for each of the formulations.

TABLE 1

Naproxen Na Formulations Particle Size

| Formulation | Particle Diameter Mean ± SD (n) | Fines Present in Sample |
|---|---|---|
| #2 | 435 ± 256 (58) | 435 particles < 100 µm in diameter |
| #4 | 420 ± 133 (70) | 75 particles < 179 µm in diameter |

The particle size distribution for Formulation 2 exhibits a wider range of particle sizes as well as more "fines" present in the sample as a proportion of the total number of particles examined (FIG. 6). The particle distribution for Formulation 4 exhibits a tighter range of particle sizes as well as fewer "fines" present in the sample as a proportion of the total number of particles examined (FIG. 7).

While there may exist particle size contribution to dissolution, it is clear that Formulation 4 exhibits better control of the physical characteristics (particle size) and control of the release of naproxen Na over 4 hours. Formulation 2 exhibits greater instant release, but it is also clear that since most if not all the naproxen Na is release within 2 hours, almost all of the particles (irrespective of their size) release their naproxen Na, indicating that the composition and internal structure of the particles plays a significant role in the naproxen Na release characteristics as opposed to only size.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A particulate composition comprising
   (a) a biologically active core, said biologically active core comprising
      (i) naproxen, a pharmaceutically acceptable salt of said naproxen, or a combination thereof and
      (ii) a drug binding polymer comprising a silicified high density microcrystalline B cellulose composed of 98% microcrystalline cellulose and 2% colloidal silicon dioxide, wherein said naproxen, said pharmaceutically acceptable salt of said naproxen, or said combination thereof is in reversible association with said drug binding polymer and in a weight ratio therewith of from about 20:1 to about 1:2; and
   (b) a coat, said coat comprising a membrane-forming polymer, said membrane-forming polymer comprising ethylcellulose and surrounding said biologically active core, wherein the particulate composition comprises microparticles/microparticulates having average diameter of from about 100 µm to about 900 µm;
   wherein the particulate composition has a dissolution rate which when measured in a type 1 dissolution basket apparatus according to U.S. Pharmacopoeia XXII in phosphate buffer at pH 7.2 and at 75 r.p.m. corresponds to the following dissolution pattern
   (1) from 15 to 50% of the total amount of said naproxen, said pharmaceutically acceptable salt of said naproxen, or said combination thereof is released after 0.5 hours of measurement in said apparatus;
   (2) from 25 to 75% of the total amount of said naproxen, said pharmaceutically acceptable salt of said naproxen, or said combination thereof is released after 1 hour of measurement in said apparatus; and
   (3) not less than 65% of the total amount of said naproxen, said pharmaceutically acceptable salt of said naproxen, or said combination thereof is released after 4 hours of measurement in said apparatus.

2. The particulate composition according to claim 1, wherein the biologically active core further comprises a set of one or more drug binding polymers selected from the group consisting of cellulose acetate, cellulose propionate, cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly (ethylene), poly(ethylene) low density, poly(ethylene) high density, poly(propylene), poly(ethylene oxide), poly(ethylene terephthalate), poly(vinyl isobutyl ether), poly(vinyl acetate), poly(vinyl chloride) and polyurethane and combinations thereof.

3. The particulate composition according to claim 1, wherein said reversible association between said naproxen, said pharmaceutically acceptable salt of said naproxen, or said combination thereof and said drug binding polymer comprises chemical bonding, ionic bonding, complexation, van der Waals interaction, hydrogen bonding, or combinations thereof.

4. The particulate composition according to claim 2, wherein at least one of said set of one or more drug binding polymers is insoluble in water.

5. The particulate composition according to claim 2, wherein at least one of said set of one or more polymers is soluble in water.

6. The particulate composition according to claim 2, wherein said coat further comprises a water-insoluble, water-permeable polymer capable of retarding drug release.

7. The particulate composition according to claim 2, wherein said biologically active core comprises a powder, said powder comprising particles of said naproxen, said pharmaceutically acceptable salt of said naproxen, or said combination thereof mixed with particles of said set of one or more drug binding polymers, wherein said set of one or more drug binding polymers comprises at least one pharmaceutically acceptable water insoluble polymer.

8. A particulate composition comprising
   (a) a biologically active core, said biologically active core comprising
      (i) naproxen, a pharmaceutically acceptable salt of said naproxen, or a combination thereof and (ii) a drug binding polymer consisting of a silicified high density microcrystalline cellulose composed of 98% microcrystalline cellulose and 2% colloidal silicon dioxide, wherein said naproxen, said pharmaceutically acceptable salt of said naproxen, or said combination thereof is in reversible association with said drug binding polymer and in a weight ratio therewith of from about 20:1 to about 1:2; and (b) a coat, said coat comprising a membrane-forming polymer, said membrane-forming polymer comprising ethylcellulose and surrounding said biologically active core, wherein the particulate composition comprises microparticles/microparticulates having average diameter of from about 100 µm to about 900 µm;

wherein the particulate composition has a dissolution rate which when measured in a type 1 dissolution basket apparatus according to U.S. Pharmacopoeia XXII in phosphate buffer at pH 7.2 and at 75 r.p.m. corresponds to the following dissolution pattern (1) from 15 to 50% of the total amount of said naproxen, said pharmaceutically acceptable salt of said naproxen, or said combination thereof is released after 0.5 hours of measurement in said apparatus;

(2) from 25 to 75% of the total amount of said naproxen, said pharmaceutically acceptable salt of said naproxen, or said combination thereof is released after 1 hour of measurement in said apparatus; and (3) not less than 65% of the total amount of said naproxen, said pharmaceutically acceptable salt of said naproxen, or said combination thereof is released after 4 hours of measurement in said apparatus.

9. A particulate composition comprising (a) a biologically active core, said biologically active core consisting of (i) naproxen, a pharmaceutically acceptable salt of said naproxen, or a combination thereof and (ii) a silicified high density microcrystalline cellulose composed of 98% microcrystalline cellulose and 2% colloidal silicon dioxide, wherein said naproxen, said pharmaceutically acceptable salt of said naproxen, or said combination thereof is in reversible association with said silicified high density microcrystalline cellulose and in a weight ratio therewith of from about 20:1 to about 1:2; and (b) a coat, said coat comprising a membrane-forming polymer, said membrane-forming polymer comprising ethylcellulose and surrounding said biologically active core, wherein the particulate composition comprises microparticles/microparticulates having average diameter of from about 100 µm to about 900 µm;

wherein the particulate composition has a dissolution rate which when measured in a type 1 dissolution basket apparatus according to U.S. Pharmacopoeia XXII in phosphate buffer at pH 7.2 and at 75 r.p.m. corresponds to the following dissolution pattern (1) from 15 to 50% of the total amount of said naproxen, said pharmaceutically acceptable salt of said naproxen, or said combination thereof is released after 0.5 hours of measurement in said apparatus;

(2) from 25 to 75% of the total amount of said naproxen, said pharmaceutically acceptable salt of said naproxen, or said combination thereof is released after 1 hour of measurement in said apparatus; and (3) not less than 65% of the total amount of said naproxen, said pharmaceutically acceptable salt of said naproxen, or said combination thereof is released after 4 hours of measurement in said apparatus.

10. The particulate composition according to any one of claims 1 and 8, wherein said biologically active core comprises a powder, said powder comprising particles of said naproxen, said pharmaceutically acceptable salt of said naproxen, or said combination thereof mixed with particles of said drug binding polymer.

11. The particulate composition according to any one of claims 1, 8, and 9, wherein the composition is a once daily solid controlled-release oral dosage form.

12. The particulate composition according to any one of claims 1, 8, and 9, wherein the composition is a twice a day solid controlled-release oral dosage form.

13. The particulate composition of any one of claim 1, 8, or 9, wherein said particulate composition comprises microparticles/microparticulates having average diameter selected from the group consisting of from 100 µm to about 150 µm; from about 150 µm to about 200 µm; from about 200 µm to about 250 µm; from about 250 µm to about 300 µm; from about 300 µm to about 350 µm; from about 350 µm to about 400 µm; from about 400 µm to about 450 µm; from about 450 µm to about 500 µm; from about 500 µm to about 550 µm; from about 550 µm to about 600 µm; from about 600 µm to about 650 µm; from about 650 µm to about 700 µm; from about 700 µm to about 750 µm; from about 750 µm to about 800 µm; from about 800 µm to about 850 µm; from about 850 µm to about 900 µm; from about 150 µm to about 200 µm; from about 200 µm to about 250 µm; from about 250 µm to about 300 µm; from about 300 µm to about 350 µm; from about 350 µm to about 400 µm; from about 400 µm to about 450 µm; from about 450 µm to about 500 µm; from about 500 µm to about 550 µm; from about 550 µm to about 600 µm; from about 600 µm to about 650 µm; from about 650 µm to about 700 µm; from about 700 µm to about 750 µm; from about 750 µm to about 800 µm; from about 800 µm to about 850 µm; from about 200 µm to about 250 µm; from about 250 µm to about 300 µm; from about 300 µm to about 350 µm; from about 350 µm to about 400 µm; from about 400 µm to about 450 µm; from about 450 µm to about 500 µm; from about 500 µm to about 550 µm; from about 550 µm to about 600 µm; from about 600 µm to about 650 µm; from about 650 µm to about 700 µm; from about 700 µm to about 750 µm; from about 750 µm to about 800 µm; from about 250 µm to about 300 µm; from about 300 µm to about 350 µm; from about 350 µm to about 400 µm; from about 400 µm to about 450 µm; from about 450 µm to about 500 µm; from about 500 µm to about 550 µm; from about 550 µm to about 600 µm; from about 600 µm to about 650 µm; from about 650 µm to about 700 µm; from about 700 µm to about 750 µm; from about 300 µm to about 350 µm; from to about 350 µm to about 400 µm; from to about 400 µm to about 450 µm; from to about 450 µm to about 500 µm; from to about 350 µm to about 400 µm; from about 400 µm to about 450 µm; from to about 450 µm to about 500 µm and combinations thereof.

14. A pharmaceutical formulation, said pharmaceutical formulation comprising the particulate composition of claim 1, 8, or 9 filled into capsules or compressed into tablets.

15. The composition of any one of claim 1, 8, or 9, wherein said particulate composition has a particle size distribution selected from the group consisting of about 60% of the particles having a particle diameter of about 1267 µm or less; 58% of particles having a particle diameter of about 1055 µm or less; about 53% of particles having a particle diameter of about 949 µm or less; about 52% of particles having a particle diameter of about 737 µm or less; about 50% of particles having a particle diameter of about 631 µm or less; about 47% of particles having a particle diameter of about 525 µm or less; about 37% of particles having a particle diameter of about 419 µm or less; about 21% of particles having a particle diameter of about 313 µm or less; and about 6% of particles having a particle diameter of about 207 µm or less.

16. The composition of any one of claim 1, 8, or 9, wherein said particulate composition has a particle size distribution selected from the group consisting of about 80% of the particles having a diameter of about 860 µm or less; about 77% of particles having a particle diameter of about 798 µm or less; about 75% of particles having a particle diameter of about 736 µm or less; about 69% of particles having a particle diameter of about 674 µm or less; about 65% of particles having a particle diameter of about 612 µm or less; about 61% of particles having a particle diameter of about 550 µm or less; about 52% of particles having a particle diameter of about 488 µm or less; about 37% of particles having a particle diameter of about 426 µm or less; about 26% of particles having a particle diameter of about 364 µm or less; about 10% of particles having a particle diameter of about 302 µm or less; and about 5% of particles having a particle diameter of about 240 µm or less.

17. The composition of any one of claim 1, 8, or 9, wherein the coat is produced by spraying a solution of the membrane-forming polymer at a rate of 15 g per minute and at 20-25° C.

\* \* \* \* \*